United States Patent
Ombrellaro

(10) Patent No.: US 6,726,638 B2
(45) Date of Patent: Apr. 27, 2004

(54) DIRECT MANUAL EXAMINATION OF REMOTE PATIENT WITH VIRTUAL EXAMINATION FUNCTIONALITY

(75) Inventor: Mark P. Ombrellaro, Bellevue, WA (US)

(73) Assignee: Cel-Kom LLC, Bellevue, WA (US)

( * ) Notice: Subject to any disclaimer, the term of this patent is extended or adjusted under 35 U.S.C. 154(b) by 0 days.

(21) Appl. No.: 10/274,569

(22) Filed: Oct. 18, 2002

(65) Prior Publication Data

US 2003/0045815 A1 Mar. 6, 2003

Related U.S. Application Data

(63) Continuation-in-part of application No. 09/685,327, filed on Oct. 6, 2000, now Pat. No. 6,491,649.

(51) Int. Cl.[7] .......................... A61B 5/103; A61B 5/117
(52) U.S. Cl. ....................................................... 600/587
(58) Field of Search .................. 600/587, 300, 600/595, 552, 553, 554, 555; 341/20; 345/161, 145, 168, 157, 156; 128/903, 904; 434/275, 274, 262

(56) References Cited

U.S. PATENT DOCUMENTS

| | | |
|---|---|---|
| 3,428,747 A | 2/1969 | Alferieff |
| 3,742,935 A | 7/1973 | Baessler et al. |
| 3,791,375 A | 2/1974 | Pfeiffer |
| 3,974,491 A | 8/1976 | Sipe |
| 4,074,444 A | 2/1978 | Laenger, Sr. et al. |
| 4,296,756 A | 10/1981 | Dunning et al. |
| 4,337,780 A | 7/1982 | Metrick |
| 4,414,537 A | 11/1983 | Grimes |
| 4,426,884 A | 1/1984 | Polchaninoff |
| 4,444,205 A | 4/1984 | Jackson |
| 4,492,234 A | 1/1985 | Arkans |
| 4,497,184 A | 2/1985 | Utter et al. |
| 4,503,705 A | 3/1985 | Polchaninoff |
| 4,524,348 A | 6/1985 | Lefkowitz |
| 4,586,387 A | 5/1986 | Morgan et al. |
| 4,715,235 A | 12/1987 | Fukui et al. |
| 4,852,443 A | 8/1989 | Duncan et al. |
| 4,967,764 A | 11/1990 | Basser |
| 4,986,280 A | 1/1991 | Marcus et al. |
| 4,988,981 A | 1/1991 | Zimmerman et al. |
| 5,047,952 A | 9/1991 | Kramer et al. |
| 5,060,527 A | 10/1991 | Burgess |
| 5,086,785 A | 2/1992 | Gentile et al. |
| 5,119,831 A | 6/1992 | Robin et al. |
| 5,166,462 A | 11/1992 | Suzuki et al. |
| 5,181,522 A | 1/1993 | McEwen |
| 5,271,412 A | 12/1993 | Shtalryd et al. |
| 5,316,017 A | 5/1994 | Edwards et al. |

(List continued on next page.)

*Primary Examiner*—Max F. Hindenburg
*Assistant Examiner*—Brian Scott Szmal
(74) *Attorney, Agent, or Firm*—Christensen O'Connor; Johnson Kindness PLLC

(57) ABSTRACT

A simulator assembly (600) for simulating the tactile response of an item is disclosed. The simulator assembly includes a playback module (602) having sensory modulation subunits (636) operable to exert a force in response to an input signal. A tactile playback assembly (800) for translating input signals into tactile sensations upon a user is also provided. The tactile playback assembly includes a playback garment (806) having sensory modulation subunits adapted to generate a force upon a user in response to an input signal. An imaging exam assembly (900) for palpating a body and obtaining images of the body is also disclosed. An ultrasonic imaging system is further disclosed. A device for remotely conducting a direct manual examination of a patient is disclosed. A method of imparting tactile sensations to a body of a user is disclosed. A method of recording tactile data is disclosed.

17 Claims, 21 Drawing Sheets

U.S. PATENT DOCUMENTS

| | | |
|---|---|---|
| 5,339,821 A | 8/1994 | Fujimoto |
| 5,375,397 A | 12/1994 | Ferrand et al. |
| 5,381,158 A | 1/1995 | Takahara et al. |
| 5,381,805 A | 1/1995 | Tuckett et al. |
| 5,429,140 A | 7/1995 | Burdea et al. |
| 5,444,462 A | 8/1995 | Wambach |
| 5,448,996 A | 9/1995 | Bellin et al. |
| 5,449,002 A | 9/1995 | Goldman |
| 5,509,810 A | 4/1996 | Schertz et al. |
| 5,513,651 A | 5/1996 | Cusimano et al. |
| 5,515,865 A | 5/1996 | Scanlon |
| 5,533,531 A | 7/1996 | Edwards et al. |
| 5,555,894 A | 9/1996 | Doyama et al. |
| 5,562,707 A | 10/1996 | Prochazka et al. |
| 5,581,484 A | 12/1996 | Prince |
| 5,589,639 A | 12/1996 | D'Antonio et al. |
| 5,623,831 A | 4/1997 | Mesher |
| 5,662,121 A | 9/1997 | Zucker |
| 5,676,157 A | 10/1997 | Kramer |
| 5,697,165 A | 12/1997 | Richardson |
| 5,715,834 A | 2/1998 | Bergamasco et al. |
| 5,764,164 A | 6/1998 | Cartabiano et al. |
| 5,771,492 A | 6/1998 | Cozza |
| 5,775,332 A | 7/1998 | Goldman |
| 5,778,885 A | 7/1998 | Doyama et al. |
| 5,813,406 A | 9/1998 | Kramer et al. |
| 5,817,030 A | 10/1998 | Tarjan et al. |
| 5,826,578 A | 10/1998 | Curchod |
| 5,833,633 A | 11/1998 | Sarvazyan |
| 5,838,244 A | 11/1998 | Schmidt et al. |
| 5,852,258 A | 12/1998 | Tribou |
| 5,911,693 A | 6/1999 | Prochazka et al. |
| 5,916,180 A | 6/1999 | Cundari et al. |
| 5,929,782 A | 7/1999 | Stark et al. |
| 5,964,719 A | 10/1999 | Costello et al. |
| 5,964,720 A | 10/1999 | Pelz |
| 5,982,352 A | 11/1999 | Pryor |
| 5,984,880 A * | 11/1999 | Lander et al. ............. 600/595 |
| 5,986,643 A | 11/1999 | Harvill et al. |
| 5,989,199 A | 11/1999 | Cundari et al. |
| 6,004,312 A | 12/1999 | Finneran et al. |
| 6,030,347 A | 2/2000 | Nakamura et al. |
| 6,033,370 A | 3/2000 | Reinbold et al. |
| 6,035,274 A | 3/2000 | Kramer et al. |
| 6,036,660 A | 3/2000 | Toms |
| 6,042,555 A | 3/2000 | Kramer et al. |
| 6,047,259 A | 4/2000 | Campbell et al. |
| 6,049,327 A | 4/2000 | Walker et al. |
| 6,050,962 A | 4/2000 | Kramer et al. |
| 6,184,868 B1 | 2/2001 | Shahoian et al. |
| 6,186,962 B1 | 2/2001 | Lloyd et al. |
| 6,259,382 B1 | 7/2001 | Rosenberg |
| 6,310,604 B1 | 10/2001 | Furusho et al. |
| 6,385,474 B1 | 5/2002 | Rather et al. |
| 6,428,323 B1 * | 8/2002 | Pugh .......................... 434/274 |
| 2003/0031993 A1 * | 2/2003 | Pugh .......................... 434/262 |

* cited by examiner

US 6,726,638 B2

DIRECT MANUAL EXAMINATION OF REMOTE PATIENT WITH VIRTUAL EXAMINATION FUNCTIONALITY

CROSS-REFERENCE TO RELATED APPLICATION

This application is a continuation-in-part of U.S. application Ser. No. 09/685,327, filed Oct. 6, 2000, now U.S. Pat No. 6,491,649, priority from the filing date of which is hereby claimed under 35 U.S.C. §120 and the disclosure of which is hereby expressly incorporated by reference.

FIELD OF THE INVENTION

This invention relates generally to devices that process and/or obtain tactile information, and more particularly to devices that transmit, record, playback, and reproduce tactile information obtained from a remote location or time to an individual.

BACKGROUND OF THE INVENTION

During the 1980s, in an effort to overcome physician shortages in rural communities, the idea of using communications and computer systems for exchanging medical information between specialist physicians and patients separated by great distances prompted the development of "telemedicine." With the advent of the internet and inexpensive audio and video communications systems, the scope of telemedicine continues to evolve. Many physicians currently use e-mail to correspond with patients while many patients use the internet to seek out general medical information. Telemedicine systems, in their current form however, are limited by their inability to allow for the adequate performance of a physical examination.

The fundamental process of the physical exam requires a doctor to gather specific information about the patient's condition from a variety of sources (history, direct physical examination, laboratory tests, and imaging studies) then analyze that data and affect treatment. The most critical source of information comes from the actual physical examination of the patient. An expertly performed physical examination alone can be used to establish a correct diagnosis with over 90% accuracy. While some medical information can be transmitted via phone, FAX, or the internet, that derived from the actual physical contact between the doctor and patient during the manual examination process cannot, and represents the key limiting step in the entire telemedicine examination process. The inability to acquire physical data remotely, and transfer this information reliably to a physician in a non-contiguous location, limits the reliability of telemedicine for most serious medical problems.

Thus, there exists a need for a computer hardware and software system which allows for the direct manual examination of a patient in a non-contiguous location, wherein a physician may perform a manual examination of a patient's body without any actual direct physical contact between the patient and the physician. Moreover, there exists a need for a system that allows tactile and "physical contact" data to be gathered and transmitted via conventional global communications systems. Such a system would provide a means for any physician in the world to examine any patient in any location including rural or remote areas, "in the field" during an emergency or battle, or any hostile environment. There also exists a need for the transformation of applied and/or received tactile forces into digital data, which can then be transmitted over the internet, or any other type of communications platform able to transmit and receive such signals, and ultimately transmitted to a device on the other end which translates the digital signal into the appropriate output (applied) tactile force. Further, there exists a need for the recording of this digital tactile examination data, wherein the digital tactile examination data can be played back for recreation or modeling of the underlying physical characteristics of the person or object that was originally examined (interrogated) by the system.

Further still, there exists a need for an imaging exam assembly that can obtain tactile examination data simultaneously with 2-D or 3-D internal body imaging data. The inclusion of internal body imaging would allow the physician user to obtain enhanced regional anatomic information associated with the location and internal characteristics of the underlying tissues and organs being manipulated during the exam. Currently, obtaining diagnostic 2-D or 3-D body imaging requires a patient to have an additional testing component or step in the diagnostic process. Non-invasive imaging systems currently available include ultrasound, Computed Tomography (CT) scans, Magnetic Resonance Imaging (MRI), Nuclear scans, and Positron Emission Tomography (PET) scans. CT scans, PET scans, and MRIs require patients to be physically placed in a large enclosure in order to generate the study data. Ultrasound systems however are very portable and safe systems that use sound waves to generate acoustical information that can be translated into 2-D or 3-D body images. Currently ultrasound systems require either a technologist or a physician, knowledgeable in the use of ultrasound equipment, to manually place an ultrasound probe on the patient's body over the area of interest. The probe is physically connected to the ultrasound machine which provides the power and image processing systems.

The ultrasound unit emits pulses of ultrasound energy at specific frequencies that are transmitted to the body tissues. Echoes are returned from the tissues and collected by the transducer. Echoes returning from stationary tissue are detected and presented in gray scale as an image. Depth and brightness can be determined from the arrival time and signal strength characteristics of the returning echoes. Frequency changes from the returning echoes denote underlying motion of the structures below. This information is then processed by the imaging system software in order to generate an internal image of the structure being evaluated. The visual and spectral data can then be used by the physician to make diagnostic and treatment decisions. Many aspects of the ultrasound examination also require the technologist or physician user to press on the body surface with the transducer scan head in order to detect additional characteristics of the underlying structures being evaluated.

Thus there exists a need for a system operable to detect and transmit real time tactile information, as well as 2-D and 3-D ultrasound information between two individuals in non-contiguous locations. Moreover, a device that can simultaneously transmit, receive, and exchange real time tactile information data between two individuals in a non-contiguous location, as well as imaging data, to provide the user with simultaneous real time 2-D or 3-D internal or external body imaging is needed. Further, there exists a need for an enhanced medical diagnostic instrument operable to permit an end user to feel or manipulate the tissue or body structure in question as well as have the ability to view the internal impact of the applied tactile forces.

SUMMARY OF THE INVENTION

In accordance with the present invention, a simulator assembly for simulating the tactile response of an item is provided. The simulator assembly includes a playback module formed generally in the shape of at least a portion of the simulated item, the playback module body including an outer skin. The simulator assembly further includes a plurality of cavities disposed in the playback module body and beneath the outer skin. The simulator assembly also includes a plurality of sensory modulation subunits, wherein each sensory modulation subunit is disposed at least partially within one of the plurality of cavities. Also, each sensory modulation subunit is adapted to exert a force against the outer skin in response to an input signal.

The simulator assembly may include a pressure transducer adapted to generate an output signal in response to an applied force. The simulator assembly may include a computer system functionally connected to the sensory modulation subunits, wherein the computer system transmits the input signals to dynamically control the forces exerted by the sensory modulation subunits. The computer system may receive the output signals generated by the sensory modulation subunits, wherein the received output signals are used to determine the sensory modulation subunits input signals. The computer system may include a memory module containing data defining the firmness of the simulated item, wherein the data is used to determine the sensory modulation subunit input signals.

In accordance with the present invention, a tactile playback assembly for translating input signals received from a player into tactile sensations upon a user is provided. The tactile playback assembly includes an interactive pressure playback garment, the garment removably attachable to a user. The tactile playback assembly further includes a plurality of cells disposed in the garment, and a plurality of sensory modulation subunits, each sensory modulation subunit disposed within one of the cells. The sensory modulation subunits are adapted to generate a force upon the user in response to an input signal.

The tactile playback assembly may include sensory modulation subunits having a variable pressure producing device operable to generate the force upon the body of the user in response to the input signal received from the player, wherein the magnitude of the force is variable and determined by the input signal received from the player. The tactile playback assembly may include a playing device operatively linked to the sensory modulation subunits for supplying the sensory modulation subunits with the input signals. The tactile playback assembly may include a playing device that generates a video output signal, wherein the sensory modulation subunit signals are correlated with the video output signal.

In accordance with the present invention, a tactile data recording assembly is provided. The tactile data recording assembly includes an interactive pressure recording garment, the garment removably attachable to at least a portion of a user. The tactile data recording assembly also includes a plurality of cells disposed in the garment. The tactile data recording assembly also includes a plurality of sensory modulation subunits, each sensory modulation subunit housed at least partially within one of the cells, the sensory modulation subunits adapted to generate an output signal corresponding to a tactile force applied to the sensory modulation subunits. The tactile data recording assembly further includes an output signal recording device, wherein the output signal recording device is operatively linked to the plurality of sensory modulation subunits for recording the output signals generated by the sensory modulation subunits.

The sensory modulation subunits may be capable of generating an output signal of a variable magnitude such that the magnitude of the output signal is correlated to the magnitude of the tactile force applied to the sensory modulation subunits. The tactile data recording assembly may include sensory modulation subunits that include a slab of elastic material having a pressure transducer embedded therein, the pressure transducer adapted to generate a signal that is directly related to the tactile force applied to the sensory modulation subunit.

In accordance with the present invention, an imaging exam assembly for palpating a body and obtaining images of the body is disclosed. The imaging exam assembly includes a housing and an imaging device disposed at least partially within the housing, the imaging device operable to obtain images of the body. The imaging exam assembly also includes a sensory modulation subunit disposed at least partially within the housing and comprising a variable pressure-producing device, the variable pressure-producing device operable to generate a palpation pressure upon the body. The sensory modulation subunit further includes a pressure transducer, the pressure transducer adapted to generate a signal that is directly related to an interface pressure between the sensory modulation subunit and the body.

The variable pressure-producing device may further comprise an expansion chamber, wherein a pressurized fluid may be selectively directed into the expansion chamber to expand the expansion chamber to produce a desired palpation force on the body. The imaging exam assembly may further include a valve, the valve located between the expansion chamber and a pressurized fluid media reservoir, the valve operable to control the flow of the fluid media into and out of the expansion chamber. The imaging exam assembly may further include an ultrasonic transducer disposed in the housing, the transducer adapted to transmit ultrasound waves into the body. The ultrasonic transducer may also be adapted to detect ultrasound waves. The imaging exam assembly may further include a second ultrasonic transducer disposed in the housing, the second ultrasonic transducer adapted to detect ultrasound waves. The imaging exam assembly may be operable to obtain internal images of the body.

In accordance with the present invention, an ultrasonic imaging system is provided. The ultrasonic imaging system includes an ultrasound pulser and an ultrasound image display system disposed at a first location. The ultrasonic imaging system also includes an ultrasound transducer assembly that emits and detects ultrasound waves, the ultrasound transducer assembly disposed at a second location. The ultrasound transducer assembly is coupled to the ultrasound pulser and ultrasound image display system through a computer network.

In accordance with the present invention, a device for remotely conducting a direct manual examination of a patient is provided. The device includes a hand control unit having at least one first sensory modulation subunit that detects a force applied to the first sensory modulation subunit and generates a first signal in response to the detected force, and exerts a force in response to a received second signal. The device also includes a patient examination module, the patient examination module having a plurality of second sensory modulation subunits that are selectively connectable to the first sensory modulation subunit. The second sensory modulation subunit is operable to receive the first signal and exert a force in response to the received first signal. The second sensory modulation subunit is also operable to detect a force resisting the exerted force and generate the second signal based on the detected resisting force, the second signal being received by the first sensory modulation subunit. The device further includes a recording device in signal communication with the first and second sensory modulation subunits that records the first and second signals.

The device may be configured such that the first sensory modulation subunit is coupled in signal communication with a first computer and the second sensory modulation subunit is coupled in signal communication with a second computer. A communication network operatively connects the first computer with the second computer. The device may also be configured such that the hand control unit and the patient examination module are in non-contiguous locations.

In accordance with the present invention, a method of imparting tactile sensations to a body of a user is provided. The method includes wrapping a portion of a body of a user in a interactive pressure playback garment, the interactive pressure playback garment having an array of linear actuators capable of generating a tactile force upon the body of the user in response to an input signal. The method also includes connecting the interactive pressure playback garment in signal communication with a data output device capable of generating a series of input signals for transmission to the array of linear activators to selectively impart tactile forces upon the body of the user.

In accordance with the present invention, a method of recording tactile data is disclosed. The method includes wrapping a portion of a body of a user in a force detecting pad, the force detecting pad having a plurality of sensory cells capable of generating an output signal in response to a tactile force received upon the force detecting pad. The method also includes connecting the force detecting pad in signal communication with an output signal recording device. The method further includes exposing the force detecting pad to at least one force and recording the output signals generated by the tactile force receiving pad with the output signal recording device.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The device disclosed herein enables a physician to perform a direct physical examination of a patient's body without direct physical contact or proximity between the patient and the physician. This allows physical data of the type normally acquired from direct manual contact between the patient and the physician to be gathered and transmitted via conventional global communications systems. To date, "telemedicine" or the exchange of medical information between a patient and physician for the purpose of rendering a diagnosis and treatment plan, can only proceed to a point, and if the physical exam findings become critical in the decision making process, the patient is advised to actually see their personal physician or present to an emergency room where a physician can perform a physical examination. This inability to acquire physical data remotely and transfer it reliably to a physician in another location is a barrier to the evolution of medical practice and the ability of medicine to capitalize on the effectiveness and efficiencies that other business are enjoying with respect to the advances in global communications platforms and a potential global consumer audience.

As used herein, the following terms shall have the meaning indicated:

Sensory modulation subunit means any device capable of (1) detecting a force applied to the device and generating an output signal related to the detected force; and/or (2) receiving an input signal and generating a force and/or displacement related to the received input signal.

Hand control unit, or HCU, means any device adapted to contact or receive a portion of a user's body—such as a user's hand—and having sensory modulation subunits that can be accessed by the received user's hand.

Patient examination module, or PEM, means any device adapted to receive a portion of a person's (or other biological organism's) anatomy, and having sensory modulation subunits that are adjacent to the received portion of anatomy. PEMs may be used in accordance with the present invention for patient examination, but the term PEM is to be understood to also encompass devices adapted for tactile sensing of anatomy for other purposes, or for tactile sensing of other objects or substances.

Figure 1:
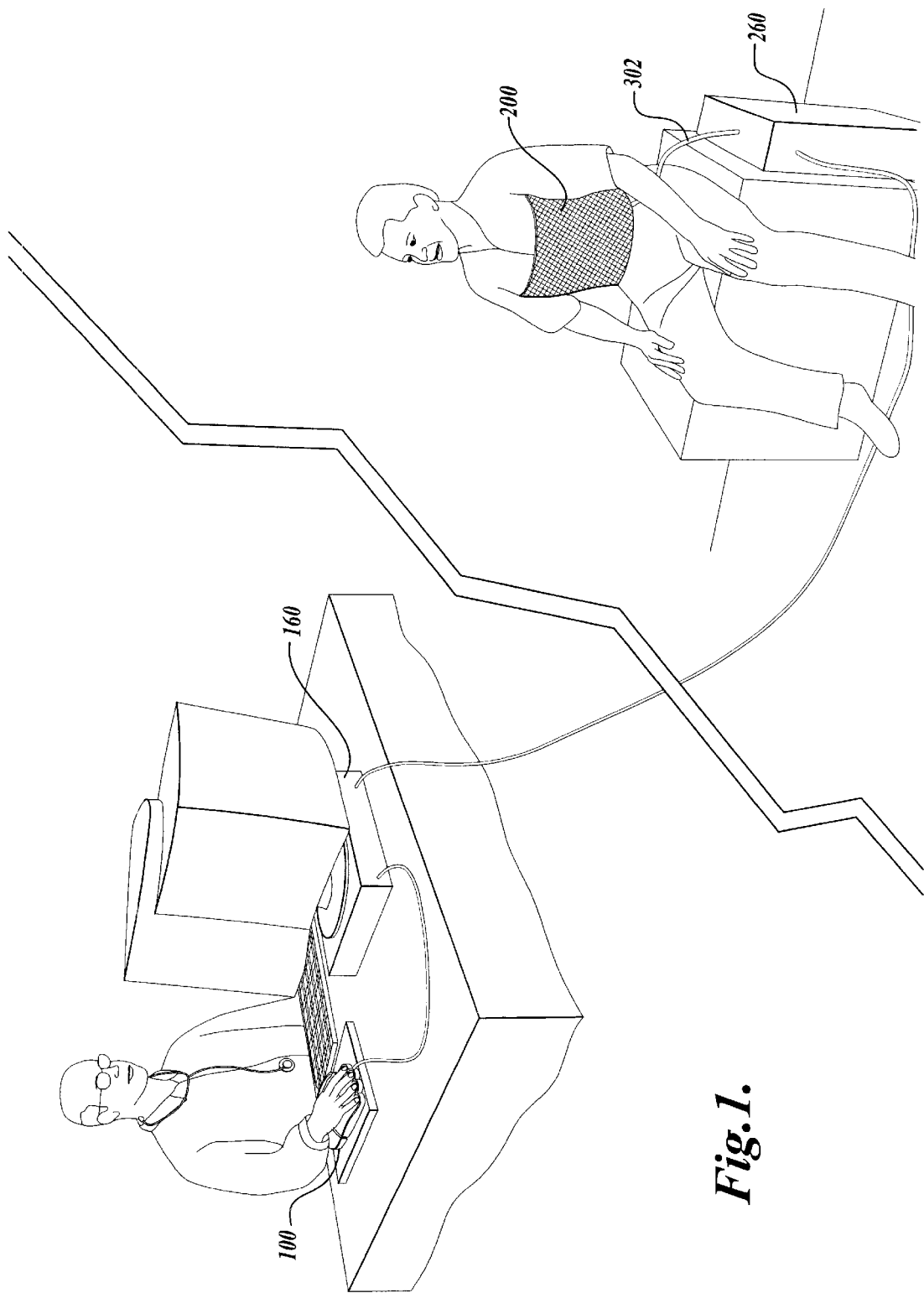
FIG. 1 illustrates a preferred embodiment of the system of the present invention in use, showing a physician examining a patient who is located remotely from the physician.

Referring now to FIG. 1, the present invention, for the remote acquisition and transmission of physically derived medical data, includes three general parts: the hand control unit 100 (HCU), the patient examination module 200 (PEM), and computer software to control the acquisition, calibration, transfer, and translation of the physical data between the physician (through the HCU) and the patient (through the PEM). The present invention allows a physician to apply hand pressures to the HCU 100 that are transmitted to a remotely situated patient and applied to selected portions of the patient's body through the PEM 200. The pressure response from the patient's body is transmitted back to the physician, thereby simulating direct contact between the physician and patient.

Hand Control Unit (HCU)

Figure 2:
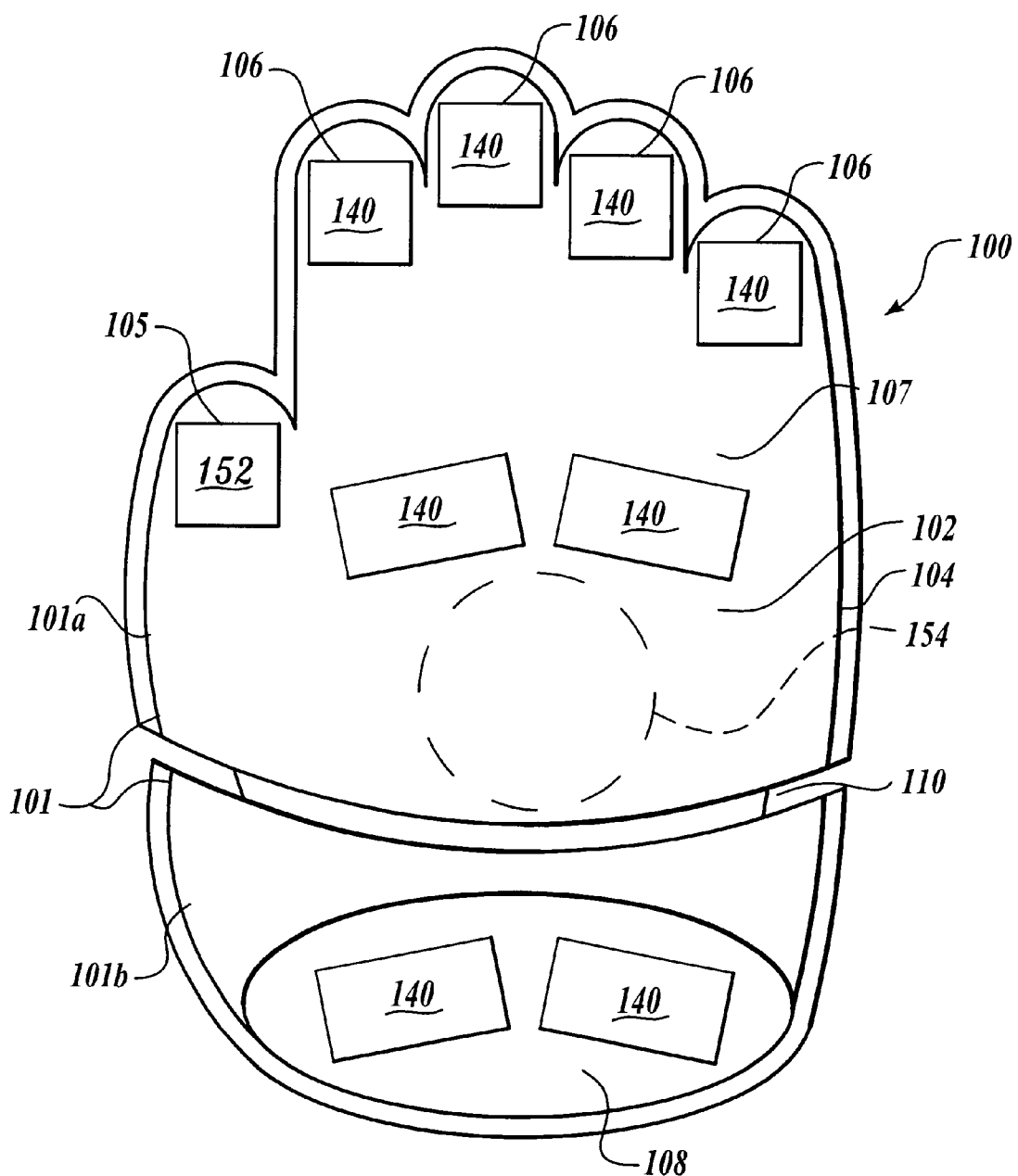
FIG. 2 is a plan view of a hand control unit in accordance with the present invention.

The HCU 100, shown in FIG. 2, has a molded plastic shell 101 formed in the shape of an actual hand. The advantages of this type of construction are that it is lightweight, easy to manufacture, durable, and impact resistant. Other materials such as wood, paper, aluminum, stone, Plexiglas™, or as of yet to be developed materials could also be used for device construction. The HCU 100 is shaped to accommodate a portion or preferably the entire inner surface of the human hand, having a palmar surface 102 including a proximal palm portion 108 and a distal palm portion 107, fingertips 106, and a thumb portion 105. An objective of any design configuration is to provide a comfortable contact surface between sensory and motor portions of the user's hand and the HCU 100. In the preferred embodiment, the HCU 100 has a slight central rise in the palmar surface 102. The periphery of the palmar surface 102 has a slight depression with respect to a border 104 of the HCU 100 to accommodate the user's hand resting comfortably on the palmar surface 102. The slight palmar rise with respect to the position of the fingertips 106 and proximal palm portion 108 (such that the level of the user's knuckles will be higher than the other parts of the fingers and hand) forms a broad based, pyramidal configuration. This design allows for maximum flexibility with respect to fingertips, distal palm, and proximal palm pressure application and reception, device control, and functionality. The HCU 100 allows for complete contact between all parts of the palmar surface of the user's palm and fingers with the palmar surface 102 of the HCU 100. In the preferred embodiment, the shell 101 of the HCU 100 is formed in two laterally disposed segments 101a, 101b, with a transverse break 110 located generally at the location of the user's mid-palmar crease. The two segments 101a, 101b, are slidably connected to permit relative longitudinal motion to allow for adjustments with respect to hand length in order to accommodate various hand sizes. Optionally, the HCU 100 could include a "glove" component (not shown) where the whole hand is inserted into a hand control unit. This would allow for contact with the top (dorsal) hand surface permitting functions related to examination motions and sensory inputs derived from the top surface of the operator's hand.

Figure 3:
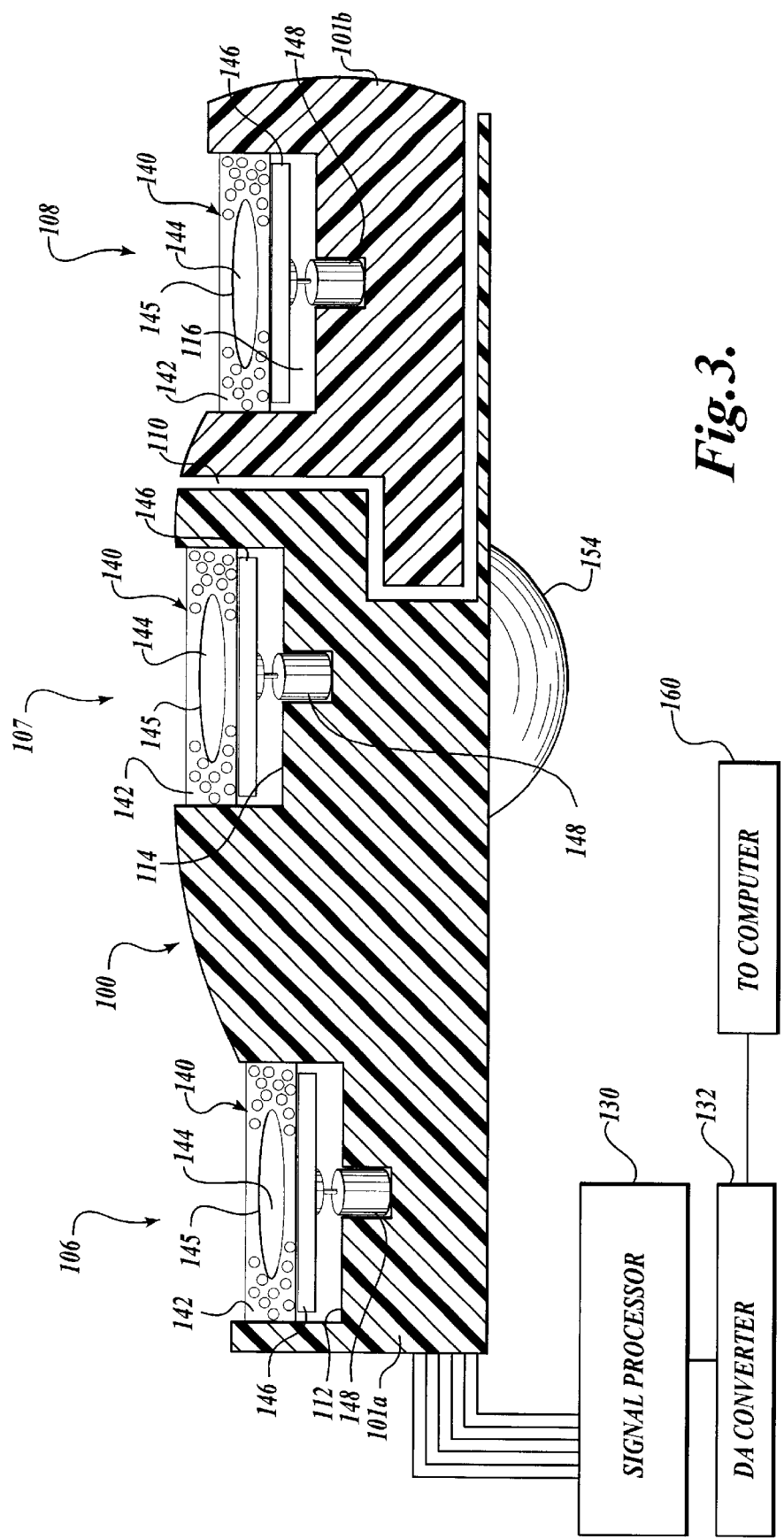
FIG. 3 is a schematic cross-sectional view of the hand control unit of FIG. 2.

Depressions or cavities 112, 114, 116, are provided in the fingertips 106, distal palm 107, and proximal palm portions 108, respectively. Within each depression 112, 114, 116, a pressure relay and reception sensory modulation subunit 140 is housed, as seen most clearly in FIG. 3. The top of the sensory modulation subunit 140 consists of a slab 142 of a pliable material such as silicon rubber or a soft plastic matrix forming a simulated skin surface. Other suitable materials may include other natural or artificial biomaterials (artificial, simulated, cultured, or engineered skin cells or substitutes) for this "skin" contact surface. The size of each slab 142 will vary with the size of each depression 112, 114, 116 in the HCU 100. In general, there are fingertip-sized sensory modulation subunits 140 for each of the fingertip 106 areas of the device, a proximal palm-sized subunit 140, and a distal palm-sized subunit 140 for the proximal palm 108 and distal palm 107 portions, respectively. To increase the sensitivity and functionality of the HCU 100, each module could be multiply subdivided and each depression could include a collection of smaller functional subunits based on the general subunit description below.

Figure 4:
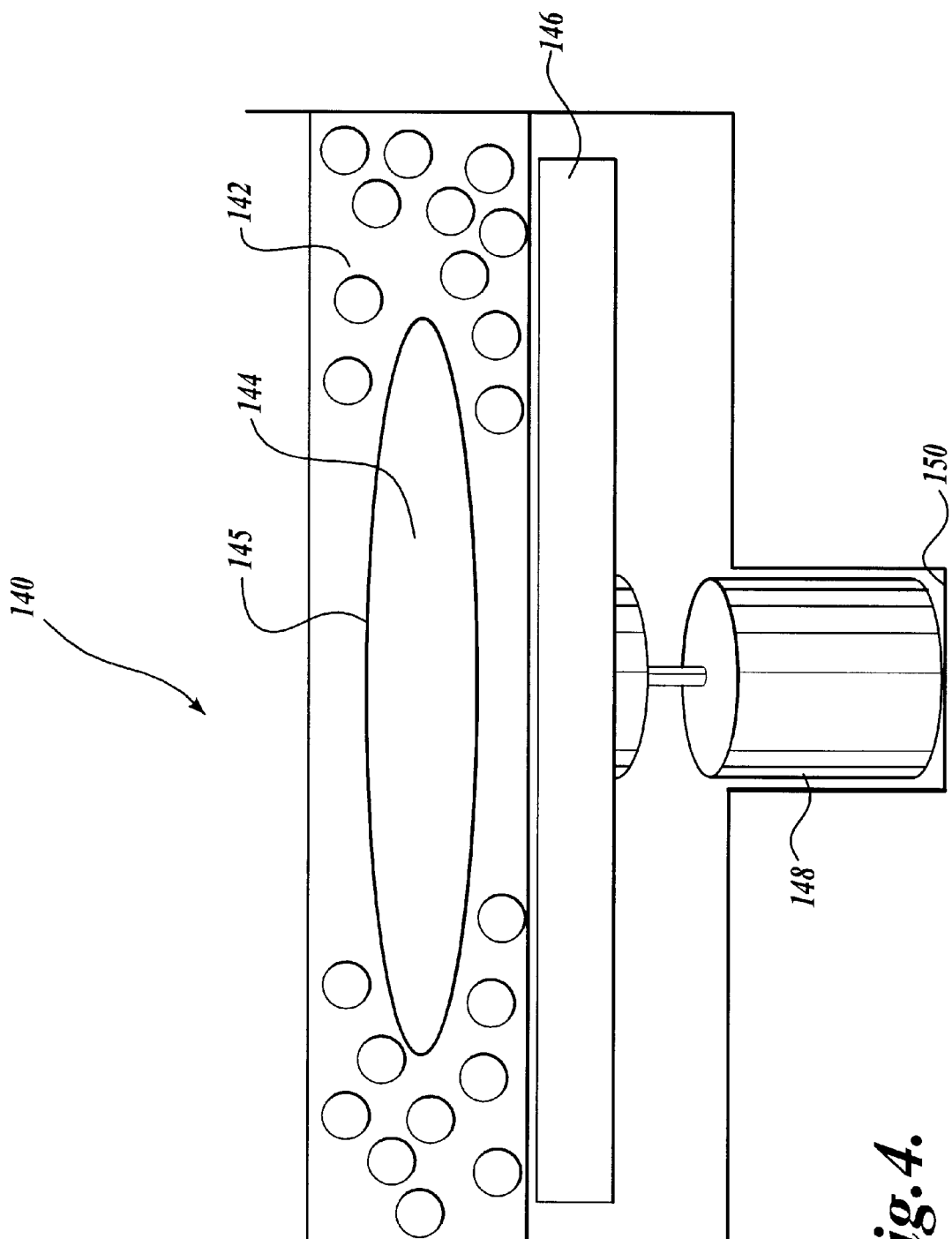
FIG. 4 is a cross-sectional sketch of a sensory modulation subunit for the hand control unit shown in FIG. 3, in accordance with the present invention.

Referring now to FIG. 4, the sensory modulation subunit 140 includes a one-way single channel pressure transducer 144 embedded within the slab 142 of simulated skin. The working surface or pressure receiving face 145 of the pressure transducer 144 is oriented upward, i.e., in the direction facing the palmar surface of the user's hand. The pressure transducer 144 is oriented such that pressure applied by the user is applied to the working surface 145 of the pressure transducer 144, while pressure or force applied from behind the transducer 144 is not sensed directly. In the preferred embodiment, a single pressure transducer 144 is located within each fingertip 106, while each palmar portion 107, 108, is subdivided into two pressure zones. Wires or other appropriate connecting mechanism (not shown) provide signal access to and from the pressure transducer 144.

The simulated skin slab 142 with the embedded single channel pressure transducer 144 is mounted on a thin support platform 146, preferably made of metal or plastic. Attached to the undersurface of the support platform 146 is a linear actuator, a variable force-producing device such as a single channel piston-type variable resistor, or other variable pressure-producing device 148. The linear actuator, or variable pressure-producing device 148, referred to herein as the "piston resistor," may be embodied in a number of ways that are known in the art, including devices that produce a variable force by electrical, mechanical, pneumatic, or hydraulic processes. A representative sampling of such devices are described, for example, in U.S. Pat. No. 5,631,861 to Kramer, illustrated in FIGS. 8a–m thereof, and referred to therein as a "finger tip texture simulator." In the preferred embodiment of the present invention, magnetically motivated devices are utilized. The piston resistor 148 provides counter pressure or a resistance force against the undersurface of the simulated skin slab 142 dependent upon the response signal derived from the patient examination module 200 (described below). The slab 142, transducer 144, support platform 146, and piston resistor 148 are disposed within the depressions 112, 114, 116, in the HCU 100. Holes 150 are provided within each depression 112, 114, 116, to accommodate insertion of the free end of the piston resistor 148. The hole 150 depth is selected such that the support platform 146 is slightly elevated from the depression lower surface and therefore the only resistance felt by the user is that of the simulated skin slab 142 itself.

Various types of pressure transducers are known in the art and suitable for use in the present invention. For example, and without limiting the scope of the present invention, U.S. Pat. No. 6,033,370 issued to Reinbold et al., discloses a capacitative pressure force transducer having a polyurethane foam dielectric sandwiched between two conductor layers. A similar device is disclosed by Duncan et al. in U.S. Pat. No. 4,852,443, wherein compressible projections on the capacitor electrodes are disposed on either side of a dielectric sheet. A pressure transducer based on variable resistance components is disclosed in U.S. Pat. No. 5,060,527 by Burgess.

Referring again to FIG. 2, the corresponding thumb portion 105 of the HCU 100 houses a button 152 for controlling and selecting functions and options related to the computer software (e.g., a mouse click control or other input device). The under surface of the HCU 100 supports a tracking ball 154 to allow for computer selection functions, and two-dimensional coordinate location of the HCU 100 in space as related to the patient through the PEM 200. It will be apparent to one of skill in the art that the button 152 and tracking ball 154 provide the basic functionality of a computer mouse and can be used to selectively interact with the computer in a familiar and well-known manner. It will also be apparent that other types of selecting mechanisms could be utilized, including touch-sensitive pads and optical systems. The HCU 100 is also linked to a signal processor 130 and an analog-to-digital/digital-to-analog signal converter 132.

The HCU 100 acts as the interface or contact point between the physician and the remote patient. The HCU 100 receives the mechanically applied pressure signal generated by the physician's hand and converts it to an electrical signal via the pressure transducer 144, while simultaneously converting the incoming electrical signal derived from the pressure response at the patient examination module 200 into a resistance signal that is applied to the piston resistor 148 mounted against the support platform. This ability of the sensory modulation subunit 140 to both "sense" the input pressure applied by the user and simultaneously provide a direct resistance feedback response to the user simulates the actual events that occur when one presses their hand against another object. Higher degrees of resistance sensed by the PEM 200 (actual patient response) in response to the direct pressure applied to the patient (as determined by the input pressure from the HCU 100) is relayed back to the HCU 100 and fed back to the physician through the piston resistor 148. Increasing resistance sensed by the PEM 200 will correspond to increasing force being applied to the undersurface of the support platform 146. This translates into a sensation of greater resistance or a "lack of give" to the simulated skin slab 142. This feedback resistance can be perceived by the user as the direct response from the patient to the forces applied by the physician.

The HCU 100 could optionally incorporate single or multiple multi-channel pressure transducer/resistor devices and/or the absolute change in resistance could be translated back to the physician's hand via the hand controller unit. The thumb portion 105, currently used for software command functions, could alternatively house a sensory modulation subunit 140. The ability to integrate thumb motions into the examination process as well as having sensory input back to this part of the hand would allow for expanded functional capacity and sensitivity of the HCU 100. The most complex embodiment of an HCU would include full contact with every portion of the operator's hand, and a large number of sensory modulation subunits 140 applied throughout the HCU. The number of subunits 140 is limited only by the ability to miniaturize these bidirectional pressure transducing devices. A large number of sensory modulation subunits would allow the user to produce and receive mechanical and sensory inputs from every portion of the operator's hand.

Patient Examination Module (PEM)

Figure 5:
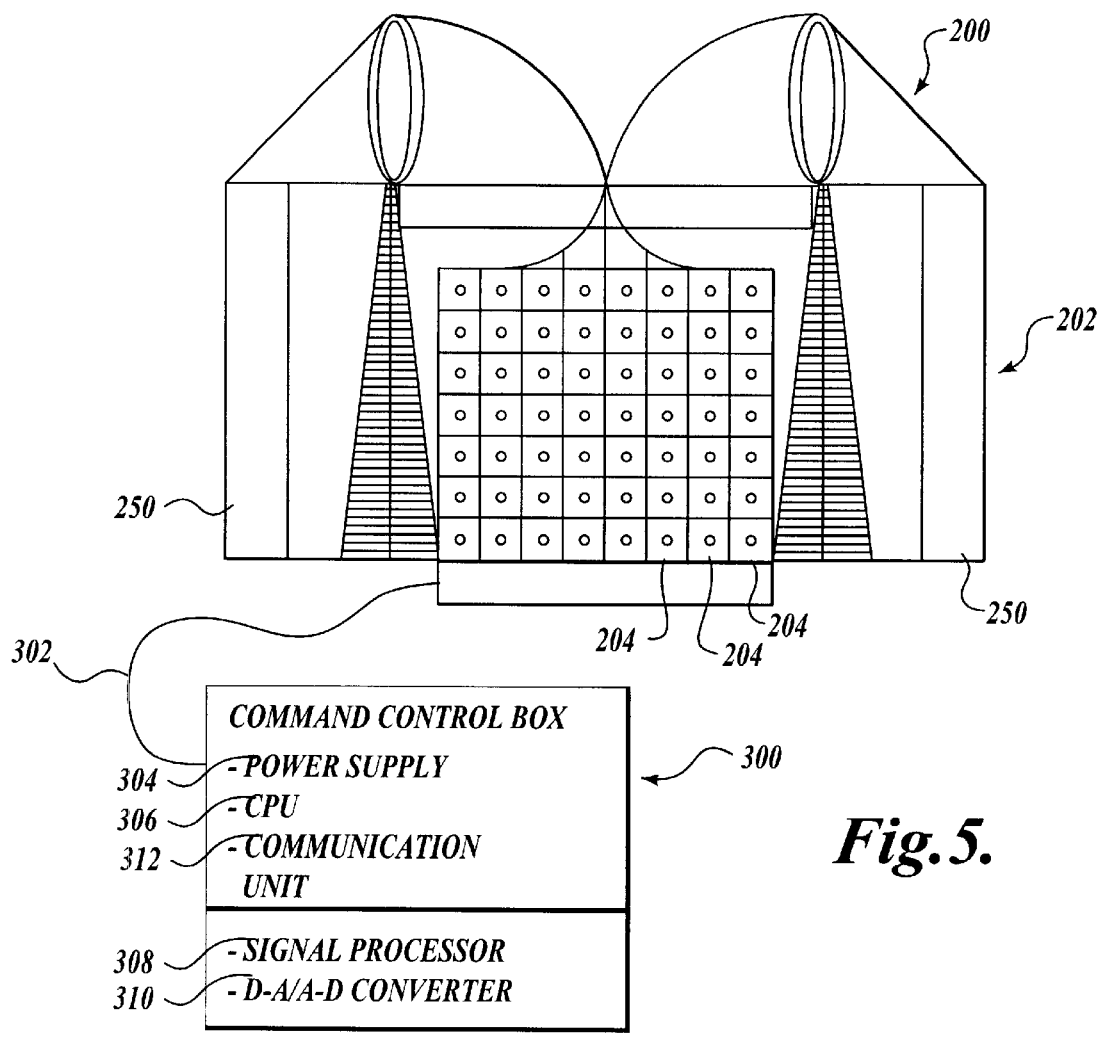
FIG. 5 is a front view of a preferred embodiment of a patient examination module for examination of a patient's torso, in accordance with the present invention.
Figure 6:
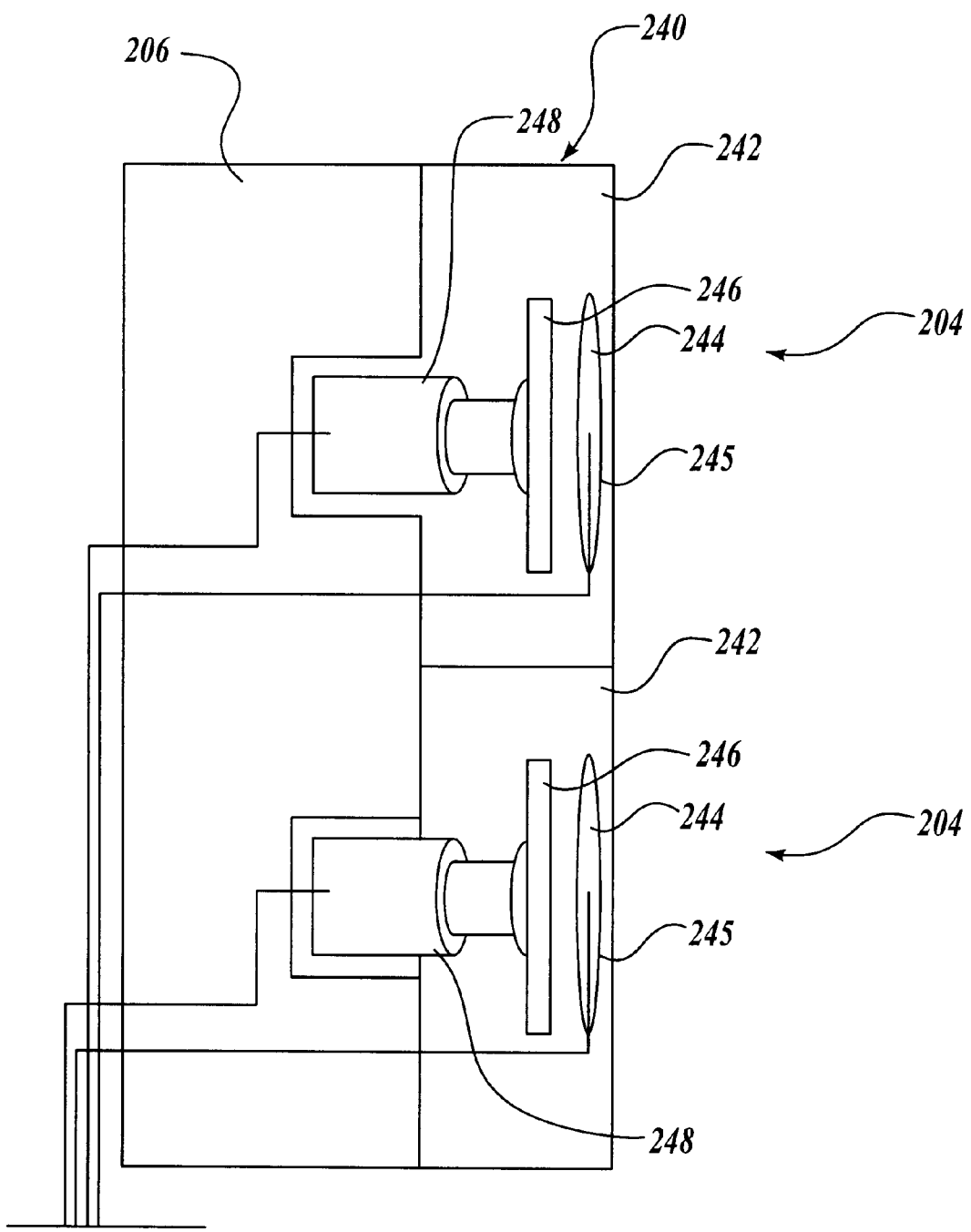
FIG. 6 is a cross-sectional view of a cell from the patient examination module shown in FIG. 5.

Referring now to FIGS. 5 and 6, PEM 200 consists of a pad or pad-like structure 202 made of soft, semi-compliant material such as nylon, rubber, silicon, or a soft plastic substrate. The entire pad 202 is solid, preferably with viscoelastic properties similar to the simulated skin slab 142 of the HCU 100. The pad 202 is subdivided into a basic structural unit called a cell or cell zone 204. The overall size of the pad 202, as well as the number of cells 204 within the pad 202, will vary depending upon the particular application. Each cell zone 204 corresponds to an area within the pad 202, preferably similar in size to the corresponding sensory modulation subunit 140 of the HCU 100. As shown in FIG. 6, a single channel pressure transducer 244 is mounted within each cell 204, oriented with the working/receiving surface 245 facing in the direction of the patient. The preferred pad 202 is a continuous gel-type structure 242 with a multitude of embedded pressure transducers 244. The back surface 206 of the pad 202 includes a flexible, semi-rigid sheeting. The currently preferred material for the back surface 206 is a plastic or polymer substance that will maintain a rigid backing to the cell zones 204, yet allow for some bending to accommodate applications to a variety of body sizes. More solid materials such as metal, wood, or composite materials could also be used as long as it provided a solid backing structure and allowed for articulation around various contoured surfaces of the body. A linear actuator, comprising a single channel piston-type variable pressure producing sensory modulation subunit 240 is attached to the undersurface of a thin support platform 246, preferably made of metal or plastic. The support platform 246 is preferably similar to the size of the fingertips 106 in the HCU 100. Centered directly below each pressure transducer 244 generally located at the interface between the cell 204 and backing 206, a piston-type variable pressure producing device 248, or similar linear actuator is embedded within the backing 206, oriented beneath the center of the support platform 246 below the pressure transducer 244.

The examination pad 202 is applied directly over the portion of the patient's body surface to be examined and held in place, for example, by a nylon loop-and-hook type of closure 250. The nylon loop-and-hook closure 250 would provide adjustability and allow for application to a wide variety of body shapes and sizes. The pad 202 could also be fashioned into vests for chest applications; binders for abdominal applications; sleeves, gauntlets, or gloves for upper extremity applications; pant legs or boots for lower extremity applications; or small strips for small applications such as fingers or toes. While the preferred embodiment of a PEM is constructed as a stationary positioned pad, a mobile sensing unit that the patient, other personnel, or a robotic guide moves over a surface of the patient's epidermis or within a body cavity, is also within the scope of the invention.

In one preferred embodiment, the PEM 200 is attached to a command control box 300 via an electrical umbilical 302. In the preferred embodiment, the command control box 300 includes a power supply 304, a small central processing unit (CPU) 306, a signal processor 308, digital-to-analog converter 310, and a communications system 312. The command control box 300 receives and transmits data to and from the PEM 200, and links the PEM 200 to the physician's HCU 100. The power supply 304 preferably allows for both the ability to work from alternating current (household or industrial) or direct current (battery operations). While an umbilical 302 is illustrated, other data links such as a wireless data link are also within the scope of the invention.

The communications system 312 of the preferred embodiment includes an internal modem (not shown) which would allow a physician's computer 160 located near the HCU 100 to connect to a remote computer 260 located near the PEM 200. Other communication systems are also possible, including systems based on: (1) light-based/optical based communications including fiber-optic cable channels and non-fiber, light based methods of data/voice/visual signal transmission; (2) wireless communications including but not limited to radio frequency, ultrahigh frequency, microwave, or satellite systems in which voice and/or data information can be transmitted or received; and (3) any future methods of voice or data transmission utilizing any currently unused mediums such as infrared light, magnetism, other wavelengths of visible and non-visible radiation, biomaterials (including biorobots or viral vectors), or atomic/subatomic particles. Optimally, the command control box 300 is connected to the pad 202 through a flexible umbilical 302 for considerations of reduced weight being applied directly to the patient, size limitations, and possibly safety (i.e., reduced RF or microwave radiation exposure from communications/data transmissions). The umbilical 302 also connects the pressure transducers 244 and variable pressure producing devices 248 within the sensory modulation subunits 240 to the power supply 304.

Other device configurations could incorporate single or multiple multi-channel pressure transducer/resistor devices and the absolute change in resistance could be translated back to the user's hand via the HCU 100. In an attempt to increase the sensitivity and functionality of the PEM 200, each cell zone 204 could be multiply subdivided and a large number of sensory modulation subunits applied throughout the PEM 200. The number of functional subunits would only be limited by the ability to miniaturize these bidirectional sensory modulation subunits. A large number of small sensory modulation subunits would provide the ability to produce and receive mechanical and sensory inputs from every portion of the PEM 200.

Figure 7:
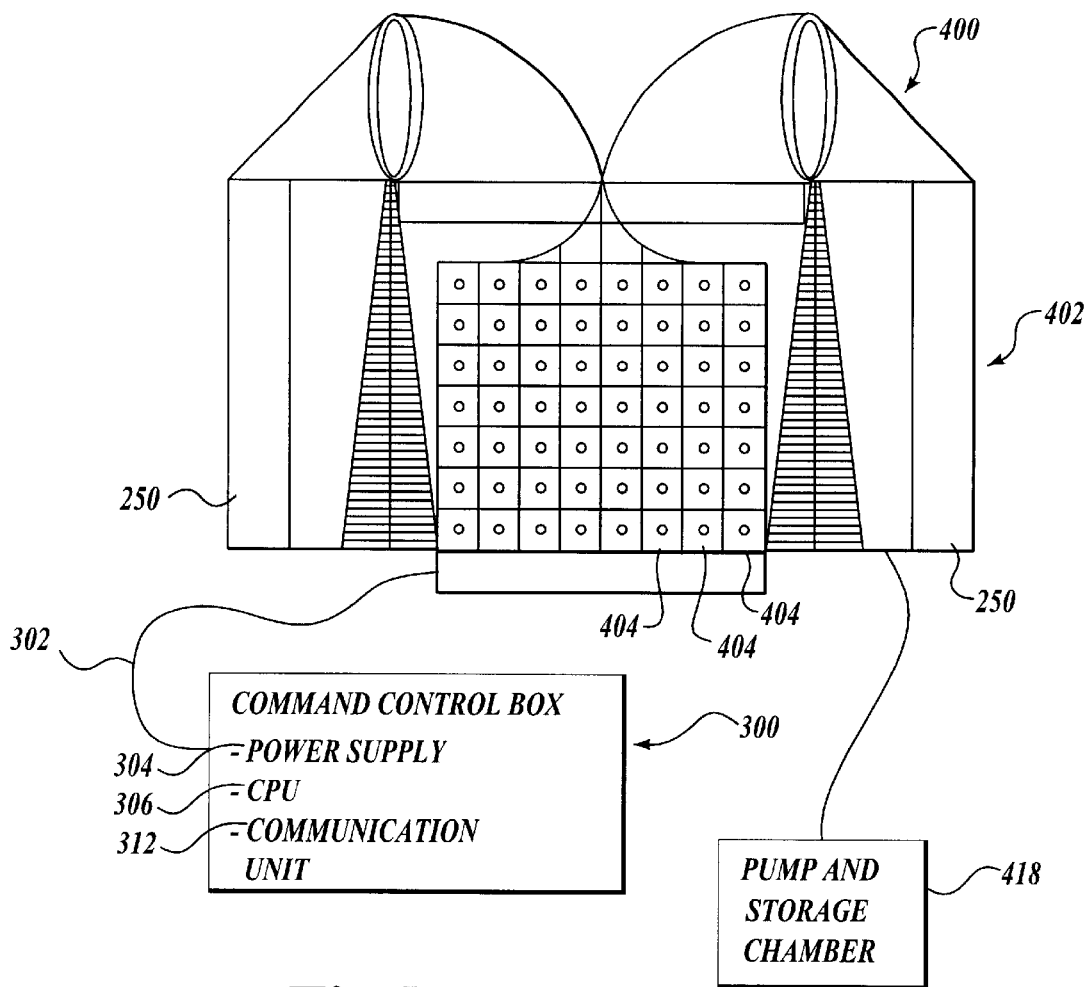
FIG. 7 is a front view of a second preferred embodiment of a patient examination module for examination of a patient's torso, in accordance with the present invention.
Figure 8:
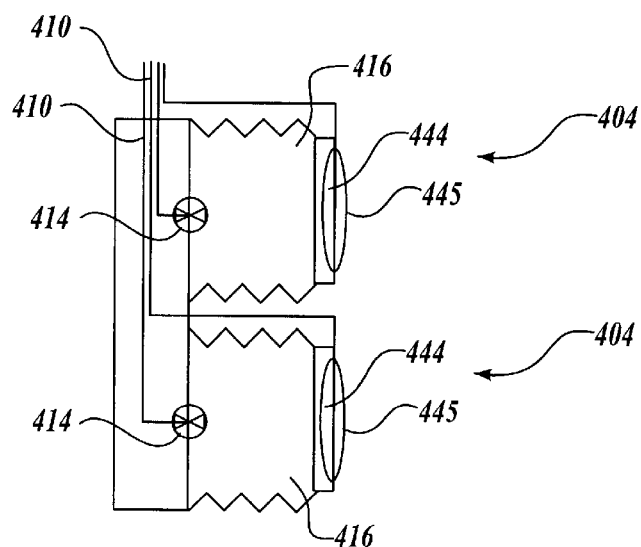
FIG. 8 is a cross-sectional view of a cell from the patient examination module shown in FIG. 7.

A second embodiment of the PEM 400 utilizes a pneumatic pressurized fluid media or hydraulic pressurized fluid media as shown in FIG. 7 and FIG. 8, rather than the electromechanical structure described above. In this second embodiment, the PEM 400 consists of a pad 402 or pad-like structure made of soft, semicompliant material such as nylon, rubber, silicon, or a soft plastic substrate. The pad 402 is subdivided into a plurality of cells 404. The overall size of the pad 402, as well as the number of cells 404 within the pad 402, will vary by device model and application. Each cell 404 is designed as an air- and water-tight hollow chamber 416 with one dual function inlet/outlet line 410 and one valve 414 to allow inflow and outflow of a pressurized fluid media, such as air, water, hydraulic fluid, or an electrochemical gel, and a single pressure transducer 444. The pressure transducer 444 is a single channel transducer similar to the transducer 144 described above for the HCU 100. The pressure transducer 444 is mounted within the material sheet applied directly to the patient's body surface. The open cell structure would therefore be behind the pressure transducer 444. The receiving surface 445 of the transducer would be oriented facing in the direction of the patient.

The pad 402 is applied directly over the portion of the patient's body surface to be examined, and is held in place, for example, by a loop-and-hook type of closure 250. The loop-and-hook closure 250 provides adjustability and allow for application to a wide variety of body shapes and sizes. The pad 402 could also be fashioned into vests, binders, sleeves, gauntlets, gloves, pant legs, boots, or small strips for small applications such as fingers or toes, as previously described. The outer surface of the pad 402 could also include a heavy reinforcing layer (i.e., lead, metal, or plastic) to provide added stability or counter pressure if required. The inlet/outlet line 410 for each cell 404 is connected to a pumping mechanism which would include a pump (not shown) and a pressurizing reservoir 418 for housing the pressurized fluid media. An intervening valve 414 is placed along the inlet/outlet line 410 between the pressure reservoir 418 and each cell 404. The PEM 400 is attached to a command control box 300 via an umbilical 302 as previously described.

Preferably this control section of the PEM 400 is disposed away from the patient for considerations of reduced weight being applied directly on the patient, size limitations if the pack is placed on a small section of the body such as a limb or finger, or possibly safety (i.e., reduced RF or microwave radiation exposure from communications/data transmissions). The specifications and functions of the command control box 300 are described above. The umbilical 302 also connects the pressure transducers 444 and the power supply 304, as well as the inlet/outlet lines 410 and valve 414 for the pressurized fluid media.

Depending upon the specific HCU 100 design, the pump and pressurizing reservoir 418 could be contained both together in the command control box 300 section, together on the PEM 400 itself, or in either area independent of one another.

A PEM 400 utilizing air as a pressurized fluid media would utilize a semi-closed circuit design. In the preferred embodiment, the pumping mechanism draws air from outside the unit into a single pressurizing reservoir 418 applied to the back of the pad 402. The pressurizing reservoir 418 is generally the same size as the pad 402. Valves 414 are located at multiple positions within the pressurizing reservoir 418 corresponding to underlying cells 404. The pressurizing reservoir 418 is therefore in direct communication with each pressure cell 404 via the intervening valve 414. A pressure regulating circuit (not shown) is integrated into the pressurizing reservoir 418 in order to sense internal chamber pressure, and relay that information back to the command control box 300 in order to ensure appropriate chamber pressure. After the appropriate cells 404 are activated, the desired pump chamber pressure achieved (corresponding to the appropriate applied pressure signal from the HCU 100), and the resulting patient response signal is transmitted back to the HCU 100 via the command control box 300, the pump vents the contents of the pressure chamber 416 back into the atmosphere via the pump. A PEM 400 utilizing a hydraulic pressurized fluid media consists of a self contained, closed fluid system circuit.

The function of the PEM 400 is to "transmit" the pressure applied by the user at the HCU 100 directly to the patient and send the resultant resistance response signal from the patient back to the physician's HCU 100. Using the software and the physician's HCU 100, various segments of the body within the confines of the PEM 400 can be examined by "selecting" the appropriate overlying cells 404 to be pressurized. The software sends the appropriate command to open the valves 414 corresponding to the selected cells 404. The number of selected cells 404 corresponds to the area of the patient's body the physician wishes to "press on" to elicit the patient's response to the applied "hand" pressure. In addition, the physician can independently select the cells or area of the body from which the return pressure data can be sent back to the user. While in many circumstances the cells which are being pressurized will also be sending the return pressure data signals back to the physician's HCU 100, for some examination functions, it is optimal to pressurize one cell set and receive from a different one.

It is also contemplated that a second HCU could be incorporated, configured to accommodate the hand opposite the first HCU, wherein the physician could use one hand to apply pressure to one location on the patient (through the first HCU and the PEM) and receive a pressure response to the other hand from another location on the patient (through the second HCU).

The computer software controls the commands for the various functions of the physician HCU 100, PEM 200 or 400, system dynamics, and the communications protocols. HCU 100 functions include cell selection functions to activate those specific cells or group of cells to be activated and the cells to transmit the resultant return signals. The software also allows for assignment of specific pressure response pads of the physician HCU 100 to be designated as send patches to transmit the physician's pressure signal as well as receive pads to transmit the patient data back to the physician.

The spatial orientation of the physician's HCU 100 with respect to the patient's body is also tracked by the computer software. Movements of the HCU 100 can be translated and sent to the PEM 200 or 400 to simulate movement of the hand across the patient's body. In addition, an anatomy database can be incorporated to provide cross-sectional anatomy and three-dimensional renderings of the specific body area being examined.

The software translates the physical pressure response applied by the physician to the HCU 100 into an electrical signal. Standardization, calibration, and real-time monitoring of the signal and signal strength are typical program functions. The software is also responsible for the transmission protocols for electrical signal conversion and transmission from the HCU 100 to the PEM 200 or 400, and vice versa. Transmission protocols include signal transmission over land-based and non-land-based communications platforms. All pump and valve commands, including pump chamber pressurization, calibration and conversion of the transmitted electrical signal back into the appropriate pressurization command correlating with a magnitude equivalent to the actual pressure applied at the hand control unit, and selected valve on/off status are also controlled by the device software.

Figure 9:
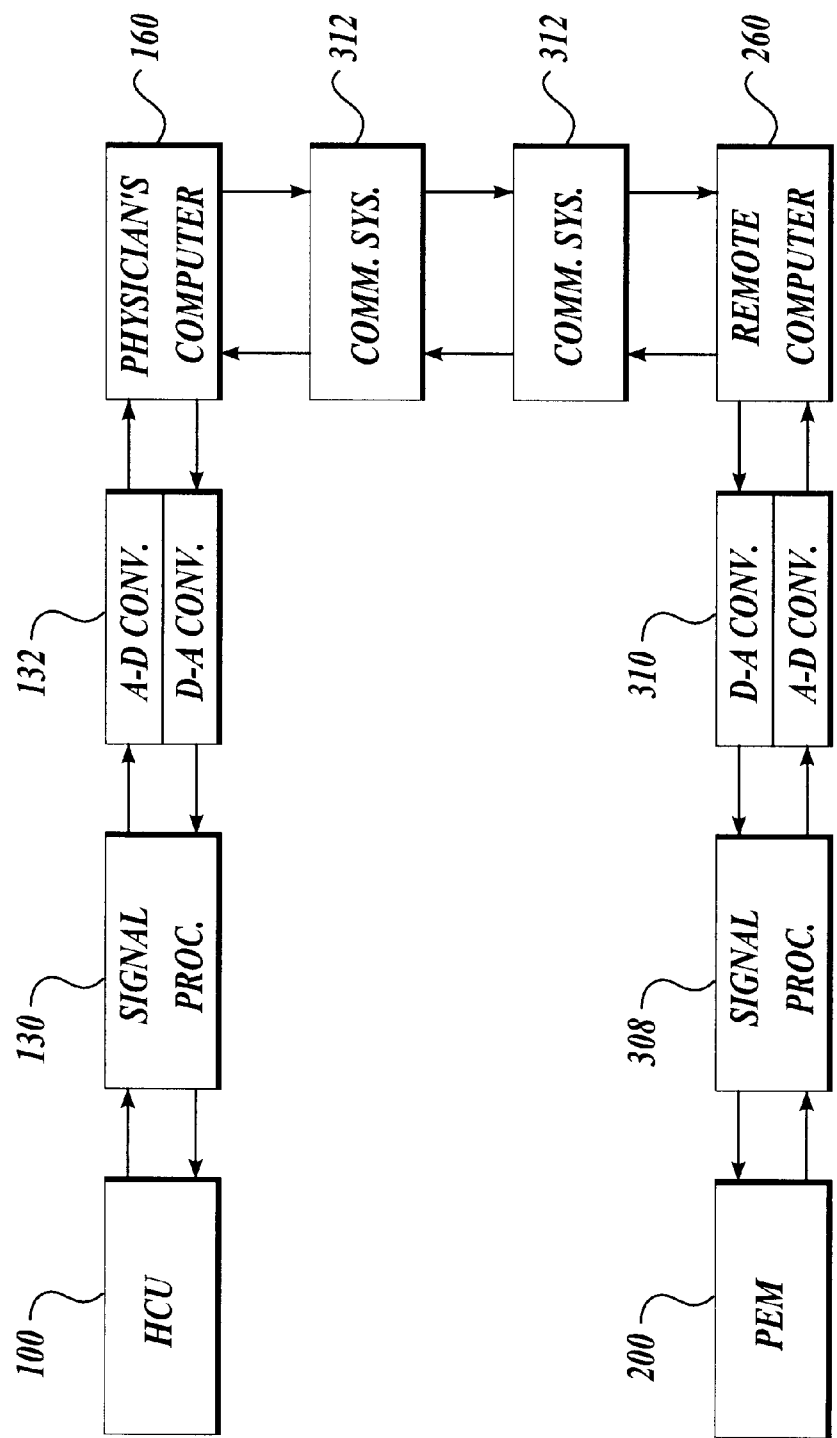
FIG. 9 is a general process flow diagram of a preferred embodiment of the present invention.

FIG. 9 represents the general process flow diagram of device functions for both the electromechanical and pneumatic/hydraulic embodiments of the present invention. Using the HCU 100, the physician selects the area of interest underlying the cells 204 or 404 to be activated corresponding to the area to be manually examined. Applying pressure to the HCU 100 via the sensory modulation subunits 140 generates signals that are sent through a signal processor 130 and analog-to-digital converter 132 to a physician's computer 160 that, in turn, sends a computer command to activate the PEM's 200 or 400 sensory modulation subunits 240 or 440 underlying the area of interest to which the HCU 100 pressure signals will be directed. The pressure transducers 244 or 444 corresponding to the area of the patient the user wishes to "feel" after the pressure stimulus is applied are then activated. This command activates the receiving cell's pressure transducers 244 or 444 so the output signal can be transmitted back to the physician's HCU 100.

The physician then presses directly on the sensory modulation subunits 140 of the HCU 100 using any combination of fingertips, proximal palmar, and distal palmar hand surfaces (ranging from a single fingertip to the whole palmar hand surface) to generate the desired input pressure stimulus equal to the force he or she would normally apply during manual examination of a patient. The applied force will vary between individuals, circumstances, and the patient areas being examined. The pressure applied by the physician against the sensory modulation subunits 140 of the HCU 100 is sensed by the pressure transducer 144 and translated into an electrical output signal. The electrical output signal is sent to the signal processor 130 and the processed analog electrical signal is converted to a digital signal 132. The digital signal is then input to a physician's computer 160.

At the physician's computer 160 the software program is responsible for software commands for linked system pathways between the various send and receive portions of the HCU 100 and the PEM 200 or 400; calibration of the signal processors 130, 308, pressure transducers 144, 244, 444, piston resistors 148, and variable pressure-producing devices 248 for both the user side and patient side equipment, and conversion of the HCU 100 electrical input signal into a corresponding PEM 200, 400 electrical output signal. If a pump system is used for the PEM 400, a pressure sensor (not shown) within the medium pressurizing reservoir 418 will be calibrated. The physician's computer 160 transmits the PEM 200, 400 electrical signal and associated software commands to the remote computer 260 via the communication systems 312. Alternatively, the patient side, or remote side, may utilize a free standing command control box 300, located near the PEM 200 or 400. The digital pressure generating signal is then converted back to an analog electrical signal 310 by a digital to analog converter, post-processed 308, then relayed to the appropriate, preselected pressure generating device of the PEM 200 or 400. The PEM 200 or 400 then applies a directed force to the patient that is based on the force applied by the user or physician to the HCU 100.

For the PEM 400, the software is responsible for receiving the incoming electrical signals from each active area of the HCU 100, assessing the corresponding magnitude of each of the input pressures applied to the various portions of the HCU 100 and converting this information into a specific pump command. The pressure commands are then transmitted to either a remote computer 260 at the patient's remote location, or directly to the command control box 300 portion of the PEM 400 previously described. The PEM 400 would then activate the pumping mechanism and pressurize the pressurizing chamber 418 in order to achieve an output pressure equal to the pressure directly applied by the physician to the HCU 100. The internal pressure of the chamber 418 is monitored by a pressure sensor that provides continuous feedback regarding the need to continue or discontinue pumping until the desired input pressure is achieved. The pressurized medium in the pressurizing chamber 418 is then transmitted to each of the selected cells 404 with open pressure valves 414 via the inlet/outlet line 410. The pressurized medium then flows into the selected cells 404 and increase the cell volume and internal cell pressure corresponding to the force applied by the physician at the HCU 100.

The downward force applied to the patient by either PEM 200 or 400 will elicit a counter-response from the patient ranging from no resistance at all and further indentation of the area being examined to great resistance or "guarding." This resistance from the patient in response to the applied force from the activated cells will be detected by the cell pressure transducer 244 or 444.

The mechanical resistance response detected by the activated pressure transducer 244 or 444 of the PEM 200 or 400 is converted into an electrical signal which is transmitted back to the command control box 300 or the remote computer 260 at the patient's location. As previously described for the input command set, this analog electrical signal will be processed 308 and converted to a digital signal 310. This digital signal is then transmitted back to the physician's computer 160 via the communications systems 312. As previously described for the HCU 100 output signal, the software program is responsible for receiving the incoming digital electrical signal(s) from each active area of the PEM 200, 400, assessing the corresponding magnitude of each of the PEM 200, 400 output pressures, and converting them into equivalent digital HCU 100 resistance signals. The digital signals are then converted to an equivalent analog electrical signal 132, post-processed 130, then directed to the appropriate preselected piston resistors of the HCU 100. The output resistance produced by the piston resistors 148 at the HCU 100 is equal to response pressure produced by the patient in response to the HCU 100 input pressure stimulus.

The counter-resistance provided by the piston resistor 148 will provide the physician with a tactile simulation of the patient's response to pressure applied over the selected area of the patient's anatomy. The system is real-time and dynamic such that the physician may simulate press-release or press-partial release maneuvers on a continuous basis within the region of preselected cells. The three key components of the device: the physician hand control unit, the computer software, and the patient examination module provide a system for a continuous, real-time, action-reaction feedback loop. It is the differential resistance between the physician's applied pressure and the patient's resistive response perceived by the physician's hand against the hand control unit that the physician can then interpret and use for medical decision-making.

Figure 10A:
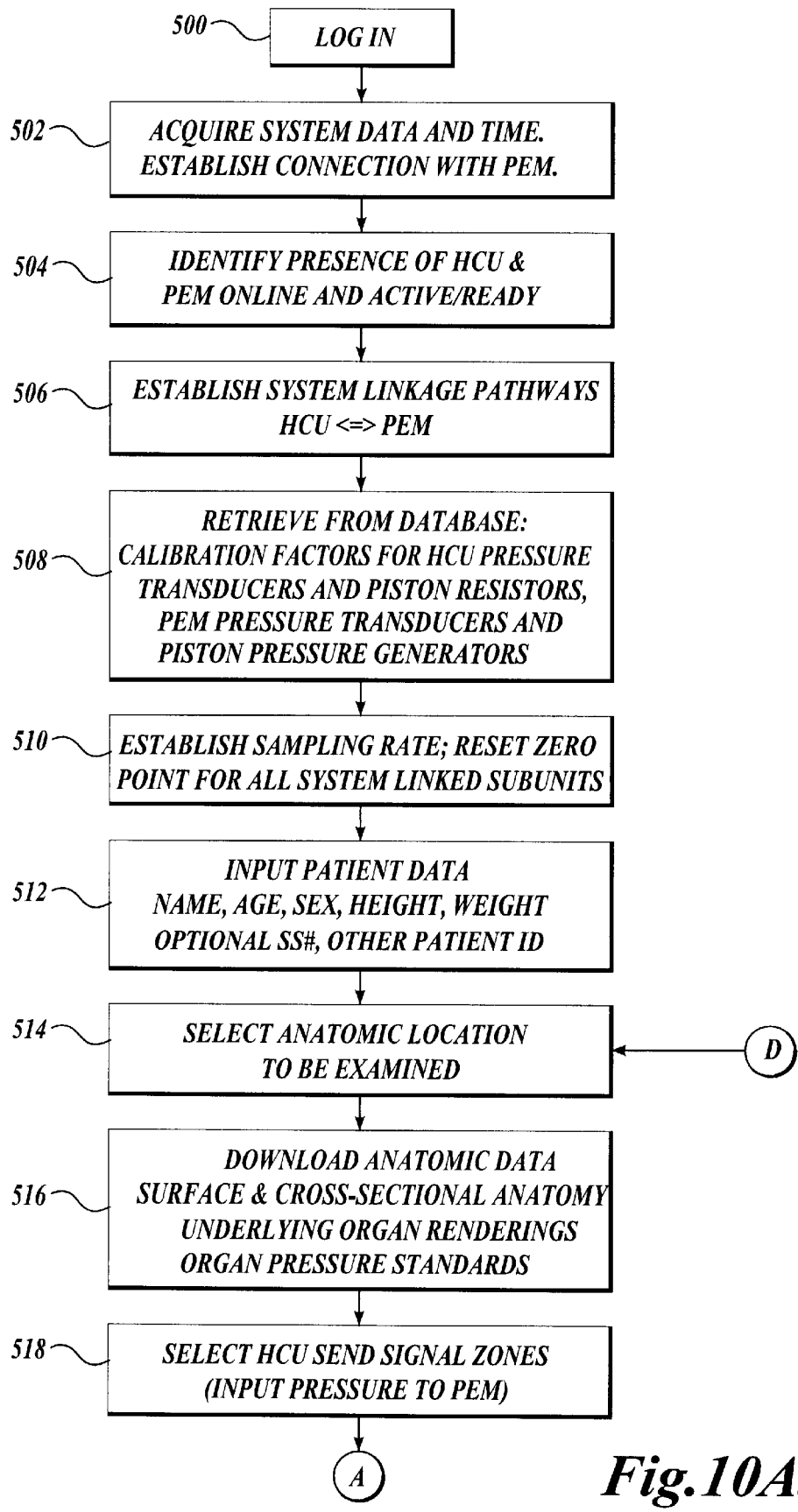
FIGS. 10A–10C present a flow diagram detailing the functions of the software controlling the preferred embodiment shown in FIG. 1.
Figure 10B:
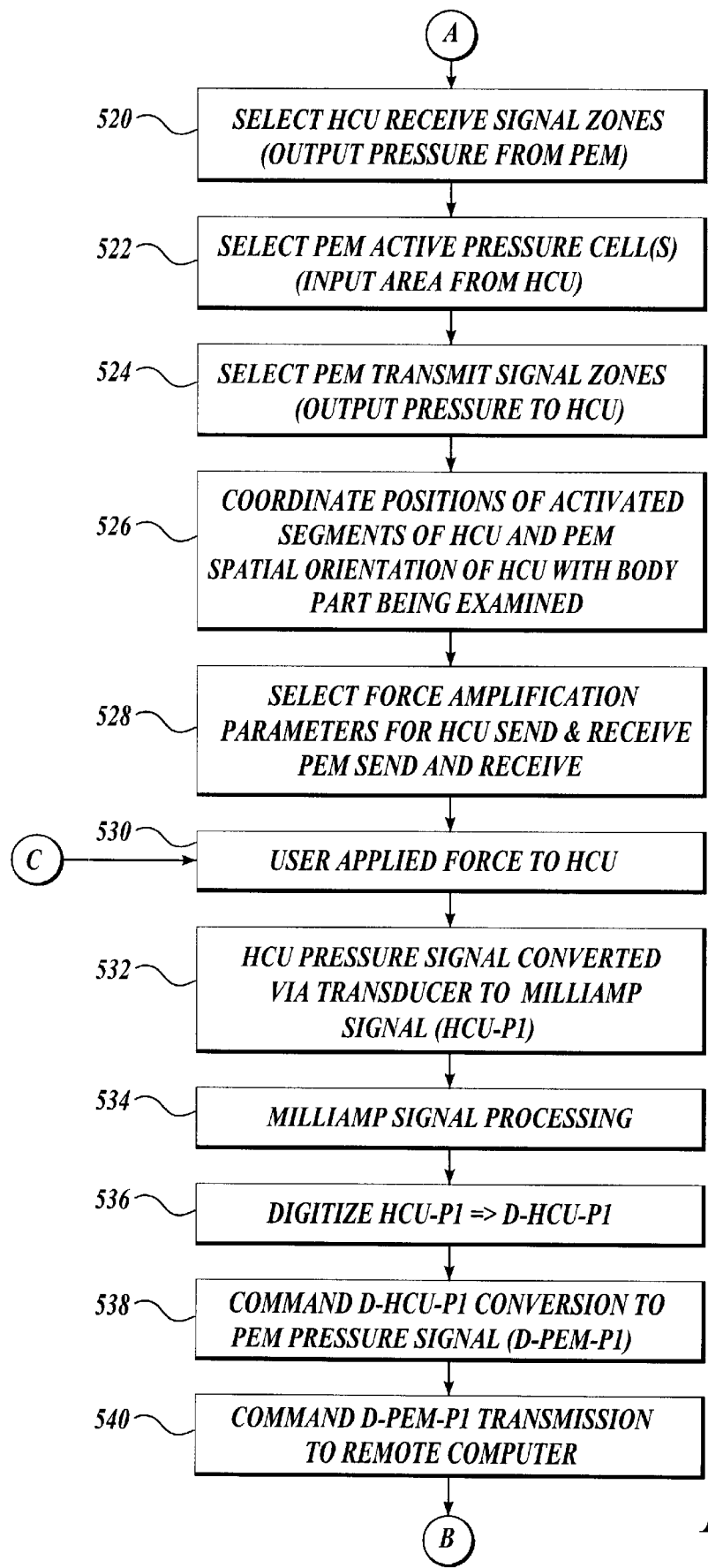
Figure 10C:
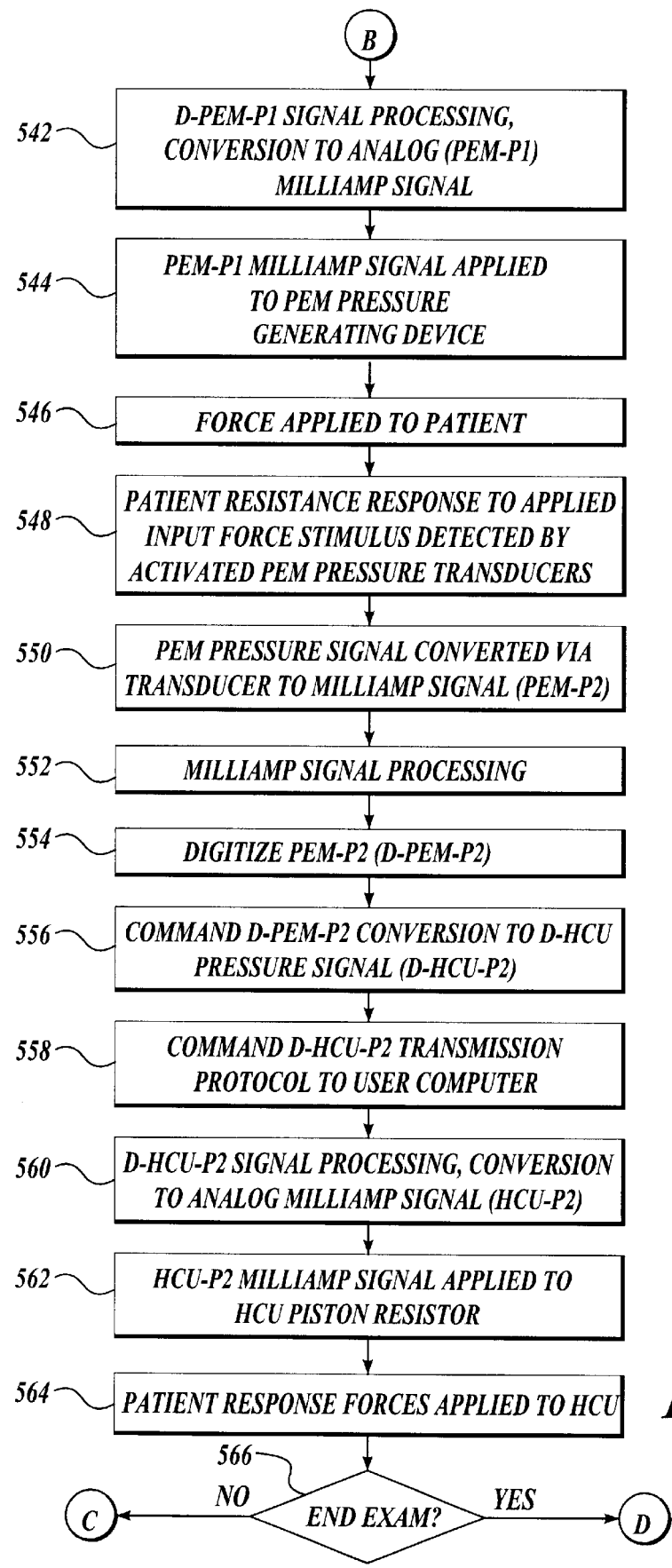

A flow chart showing the overall process that will be controlled by the software in the preferred embodiment is diagrammed in FIGS. 10A–10C. The user, generally the physician, first logs into the system 500. A mechanism for logging in is provided by any conventional means, including for example a biometric scanner in the HCU (i.e., a fingerprint reader, not shown) or a more conventional requester for a user identification and password may be provided at the physician's computer 160. The software then queries for the system date and time 502, establishes a connection with the PEM and checks the status of the HCU and PEM 504, then establishes the necessary communications links 506 therebetween. In the preferred embodiment, a first database is accessed 508 by the physician's computer 160 to obtain the various calibration factors for the HCU and PEM components, such as the pressure transducers and pressure producing devices (linear actuators). Various other initiation functions are then performed by the software 510, which functions may include establishing the sampling rates for the pressure transducers and initiating and calibrating the components (for example, establish the "zero pressure" level for the pressure transducers).

Patient identification and biometric information may then be input 512, both to verify the identity of the patent for the medical records and to establish baseline parameters that may be helpful to the examination, such as the general size and age of the patient. The physician then selects the anatomical location to be examined 514. In the preferred embodiment, a database of anatomical data is accessed 516, which may include generic still or animated pictures of the portion of the anatomy that is to be examined. It is contemplated that embodiments of the present invention may use the patient medical and biometric information, in addition to generic information relating to the portion of the anatomy that is to be examined, to adjust various system parameters, such as the sensitivity of the pressure transducers and linear actuators. The physician then selects the portions of the HCU that will provide output signals to the PEM 518, the portions of the HCU that will receive feedback pressures from the PEM 520, the cells of the PEM that will receive the pressure signals from the HCU 522, and the cells of the PEM that will send pressure signals back to the HCU 524. It is anticipated that in most applications there will be a one-to-one correspondence between the active HCU portions, and the activated PEM cells, for example, that the HCU sensory modulation subunits will send and receive pressure signals to and from the same PEM cells. However, the ability to disassociate the send and receive signals is believed to provide additional functionality to the system. The present invention contemplates systems wherein it is not possible to disassociate the HCU input and output pressure signals.

The software can also coordinate the position of the activated segments of the HCU with the PEM 526, such that movement of the HCU, in a manner similar to moving a mouse, is tracked by the system to make a corresponding change in the PEM cells that are activated. Prior to the application of any force to the system, predetermined force alteration functions can be applied 528, such as force amplification/magnification or reduction/minimization of the HCU and PEM output signals. Forces are applied to the HCU 530 by the user, and the pressure signals generate low-amperage signals 532 in the pressure transducers 144 (HCU-P1), that are sent to the signal processor to produce corresponding higher-amperage signals 534, and then converted to digital signals 536 (D-HCU-P1). The D-HCU-P1 are used to generate digital pressure signals for the PEM 538 (D-PEM-P1), and transmitted 540 from the physician's computer 160 to the remote computer 260. The D-PEM-P1 pressure signal is then converted to a low amperage analog signal (PEM-P1) 542, that is applied to the variable pressure producing device 248 of the PEM, and a corresponding force is applied to the patient 546.

The patient resistance response is detected by the selected PEM cell 548, producing a pressure response signal (PEM-P2) 550, that is processed to produce a higher amperage signal 552 and digitized (D-PEM-P2) 554. The D-PEM-P2 pressure signal is used to generate a corresponding digital pressure signal for the HCU 556, transmitted from the remote computer to the physician's computer 558, and converted to an analog signal 560 that is provided 562 to the appropriate HCU piston-type variable resister 148 to produce a responsive force at the HCU. If the examination is complete 566, then the system will reset to allow the physician to begin another exam of a different part of the patient's anatomy. Otherwise the physician can apply additional forces and detect additional responses from the patient.

Although the process has been described in terms of the preferred embodiment, it will be obvious to one of ordinary skill in the art that variations on the above process are possible. For example, an embodiment may be possible wherein the pressure signals from the pressure transducers are usable, without pre-processing to a higher amperage, or pressure transducers may be used with integral A-D converters whereby a digital signal is produced directly. Optionally, the HCU and PEM may be connected directly to a common computer or a specialized data processing system for applications where the user and the patient are in close proximity. The invention can clearly be practiced without the additional functionality provided by an anatomical database. Additionally, it will be clear to one of ordinary skill in the art how the process flow shown in FIGS. 10A–10C would be modified to accommodate the hydraulic or pneumatic embodiments of the PEM described above.

The HCU 100 is intended to enable simulation of a physical examination of a patient in a remote location. Applications within the field of medicine would include the ability to examine a patient in hostile environments such as deep sea, space, battlefield conditions, remote locations, and/or mountain/jungle expeditions. The present invention may also be adapted for non-medical and/or recreational usages, where it is desirable for an individual to examine, feel, or otherwise elicit a tactile response from another individual, body or object in a remote location.

Portable versions could also be applied, for example, in a medical station within the workplace, obviating the necessity of a patient having to actually leave work and traveling to a physicians office.

It is also contemplated that with the growing use of robotic tools for performing operations, that the above-described invention could be modified in a straightforward manner to provide a physician with tactile feedback while performing an operation using a robotic system.

Portable versions could also be applied in the home, for example to preclude the need for house calls, office visits or even after-hours trips to the emergency room. This efficiency would have a significant effect on overall health care costs.

Any application requiring tactile information or three-dimensional tactile modeling of a physical structure required by an individual in a non-contiguous location is also within the scope of the present invention.

The present invention could also be adapted to enhance the ability of the visually impaired to communicate or simulate the feel of objects without actual direct physical contact between the object and the blind individual.

First Alternate Embodiment

Figure 11:
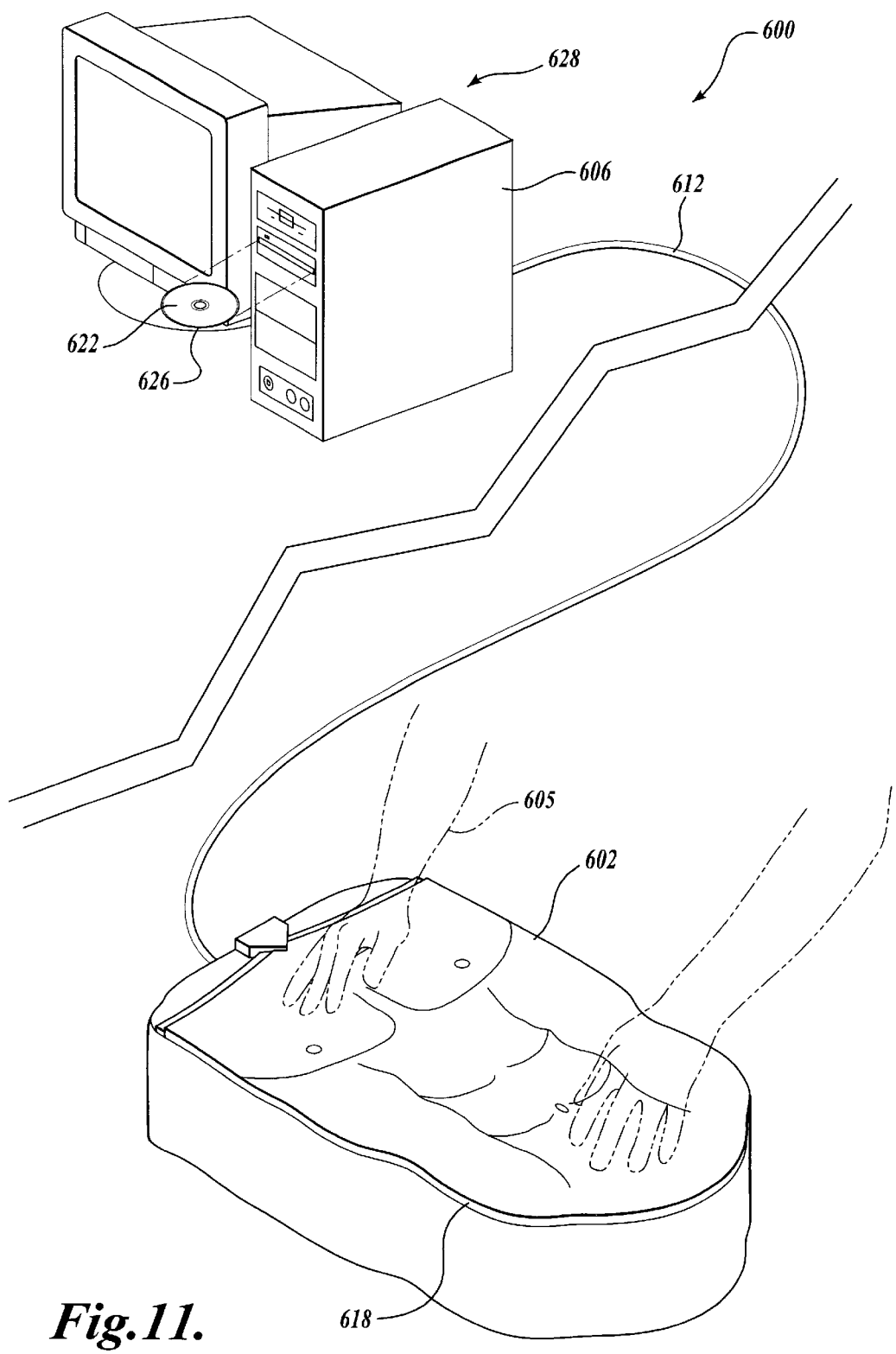
FIG. 11 is a perspective view of a first alternate embodiment formed in accordance with the present invention and generally referred to as a simulator assembly, the simulator assembly including a body-form playback module coupled to a data manipulation system by a cable.

Referring to FIG. 11, a first alternate embodiment of a simulator assembly 600 formed in accordance with the present invention is depicted. The alternate embodiment provides the ability to record and playback a tactile portion of a physical examination. As discussed below, the simulator assembly 600 contemplates that the tactile portion of the physical examination may be recorded into medical records and replayed, for example to consultants, covering physicians, patients, medico-legal situations, research, teaching, patient information, etc. The simulator assembly 600 includes a data manipulation system 628 coupled to a body-form playback module 602. The data manipulation system 628 includes a compact disk 626 (hereinafter "CD") having a digital data file 622 stored thereon, the digital data file 622 representing digitally the tactile portion of a physical exam, such as an exam performed using the HCU 100 and PEM 200 described above. The data manipulation system 628 also includes a controller, such as a well known computer 606, having computer software operable to control the calibration, translation, modeling, and/or transfer of the digital data file 622. A well known cable 612 couples the above components in signal communication.

In operation, the illustrated embodiment of the simulator assembly 600 permits prerecorded or stored digital tactile data derived from a previous exam and saved as the digital data file 622 to be played back upon the body-form playback module 602. Thus, the body-form playback module 602 may be used to represent or recreate the actual physical characteristics of a person or object previously examined at a remote time or place.

The digital data file 622 is a digital representation of a physical examination. More specifically, the digital data file 622 preferably describes a complex series of interactions between pressure sensors, optical encoders, motor commands, piston-type variable resistors, pneumatics, microcontrollers, etc. activated during the performance of a physical examination conducted with the aid of the HCUs and PEMs of the previously described embodiments. Moreover, as the original exam is conducted, the digital data describing the interactions between the pressure sensors, optical encoders, motors, piston-type variable resistors, pneumatics, and microcontrollers, etc. of the above-described HCUs and PEMs, is recorded by methods well known in the art to create the digital data file 622.

This digital data may be recorded or stored on any well known digital data storage medium, such as a CD 626, digital video disk (hereinafter "DVD"), optical disc, floppy disc, tape or any other variety of data storage media now known or to be developed, thus forming the digital data file 622. With the stored digital data file 622, the physician user now has the information suitable for use in recreating the exam findings and patient characteristics which may then be used for purposes such as medical documentation, continuity of care when checking out to on-call physicians, or as a teaching tool for medical students, residents, patients, and research.

Of note, the exact sequence of events and actions performed in conducting a physical examination are well known to those skilled in the art and therefore will not described in detail herein. Also, although in the illustrated embodiment it is preferred that the digital data sequence be obtained through the recording of digital data obtained during an actual examination, it should be apparent to one skilled in the art that the stored digital data file 622 may be derived by any suitable method well known in the art, such as by computer modeling the expected resistance to touch in various parts of the body due to a specific illness, such as the firmness in the abdomen due to appendicitis, for example.

In the illustrated embodiment, the computer software may take the stored digital data file 622 and reestablish the sequence of applied pressure values from the various portions of the physician HCU 100 and the corresponding response from the PEM 200. The sequential pattern of this action-reaction response will be mapped by the software system both with respect to time and location over the specific part of the body being examined. Anatomic location specifics are determined by reading the signature of the original PEM component used during the original examination.

Conceptually this process involves developing a dynamic 3-D model of the patient. The software will first establish from the stored digital data file 622 which PEM unit was used with the HCU. Next, the software will establish a graphic representation of the examined body part (based on the specific regional PEM used) and sequentially replay the digital data stored within the digital data file 622. The input pressure value, pressure over time function (pressure profile), stroke movement value, and component movement rate of the tactile surface of the HCU that was recorded from the original applied pressure will be mapped to the specific region of the original PEM to which that data was directed and therefore activated by the applied force. The subsequent force response detected by the PEM resulting from the force applied to the HCU will also be translated with respect to the parameters described above.

Since each PEM unit is composed of a series of smaller subunits, a grid pattern is already established over which the force and pressure data may be mapped. The series of forces applied to the HCU and PEM reaction response will then be mapped along the specific regions of the anatomy of interest. Replaying the sequence of the exam, a force and pressure profile map of the examination may be determined and a model of the underlying characteristics of the person or object that was examined may be created. This data may be downloaded into the body-form playback module 602 from a computer 606 directly attached to the body-form playback module 602 or transmitted across a communication network and downloaded to a distant computer or body-form playback module 602.

Communication networks are well known in the computer communications field. By definition, a network is a group of computers and associated devices that are connected by communications facilities or links. Network communications can be of a permanent nature, such as via cables, or can be of a temporary nature, such as connections made through telephone or wireless links. Networks may vary in size, from a local area network ("LAN") consisting of a few computers or workstations and related devices; to a wide area network ("WAN") which interconnects computers and LANs that are geographically dispersed; to a remote access service ("RAS") which interconnects remote computers via temporary communication links. An internetwork, in turn, is the joining of multiple computer networks, both similar and dissimilar, by means of gateways or routers that facilitate data transfer and conversion from various networks.

Figure 12:
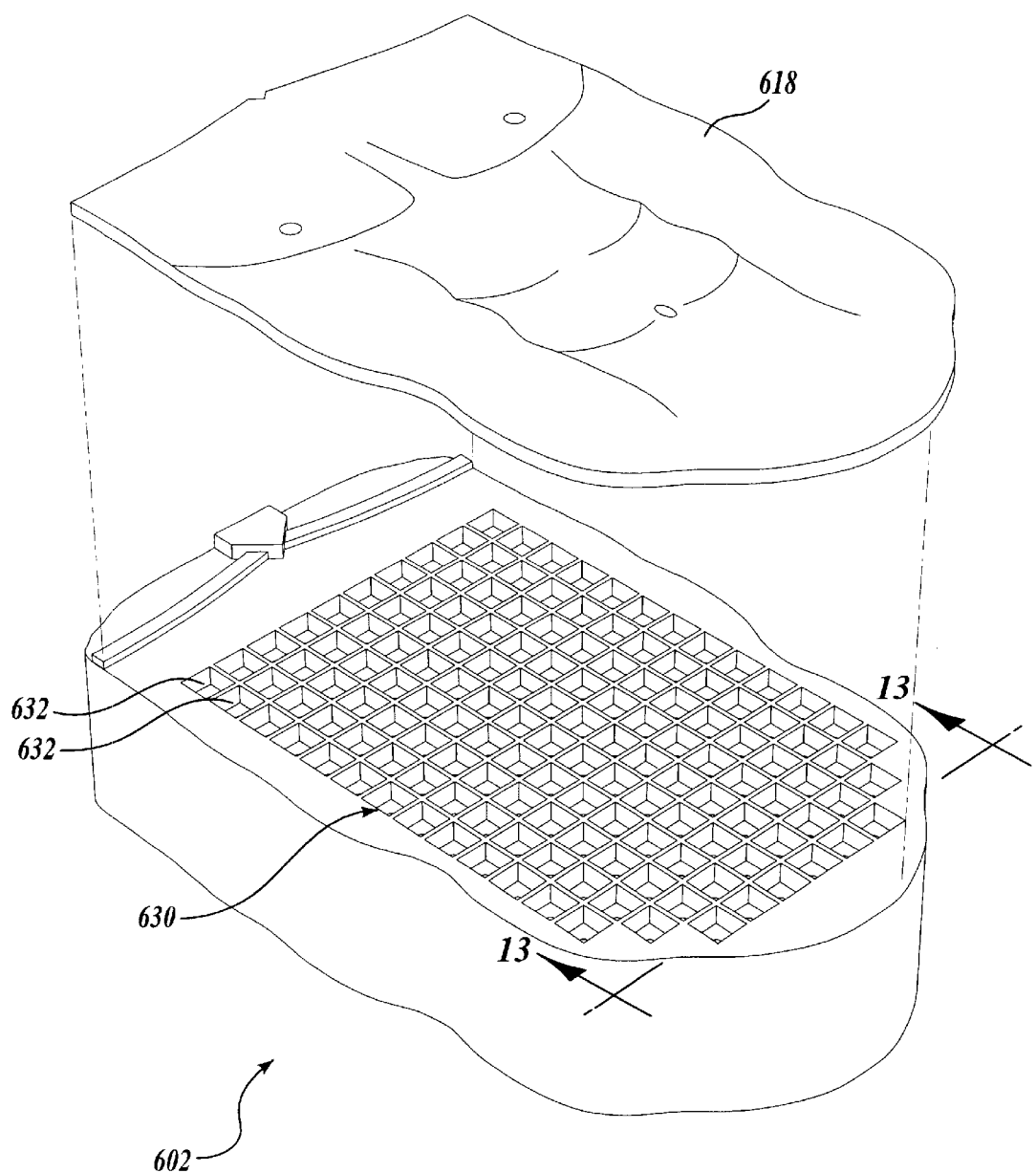
FIG. 12 is an exploded top view of the body-form playback module depicted in FIG. 11, wherein a simulated skin layer has been removed to show an underlying array of cells.
Figure 13:
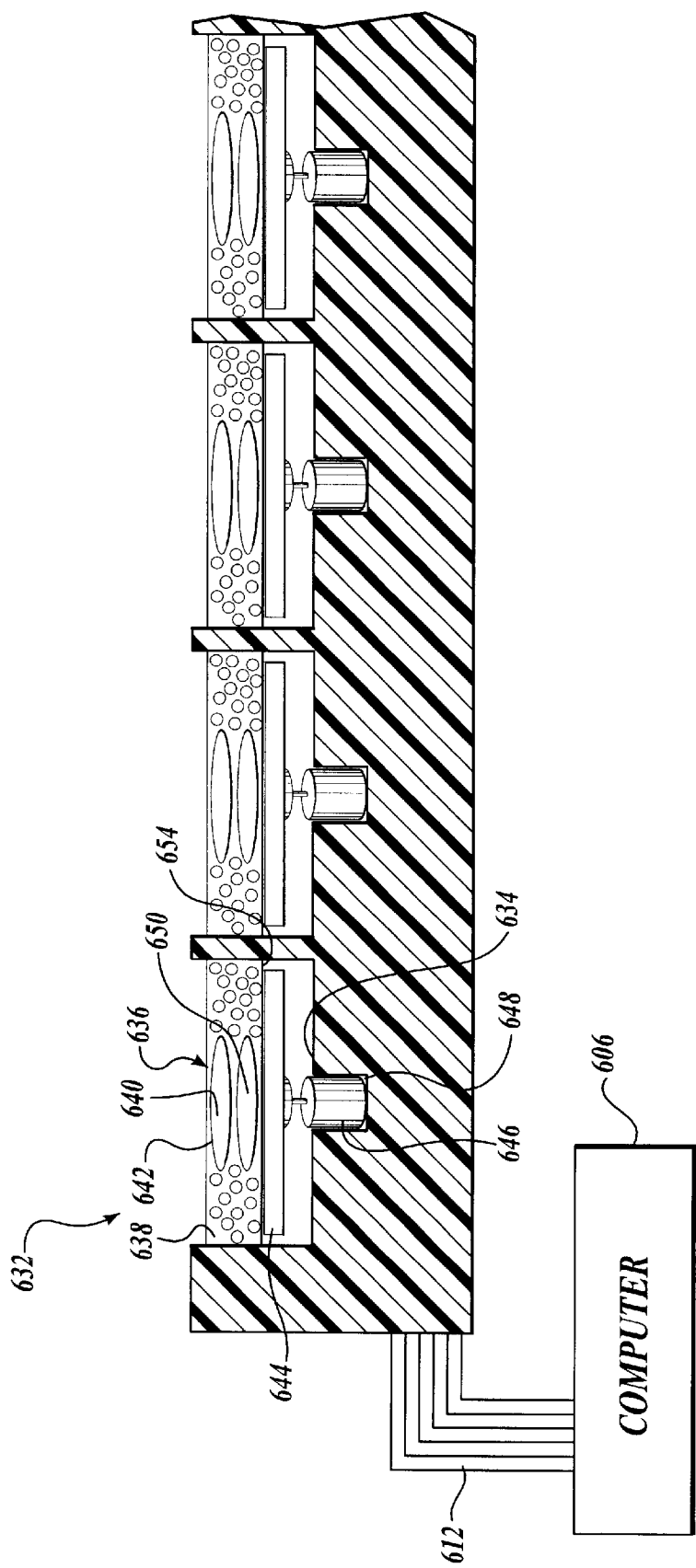
FIG. 13 is a cross-sectional view a cell of the body-form playback module depicted in FIG. 12, the cross-sectional cut taken substantially through Section 13—13 of FIG. 12, depicted with a sensory modulation subunit dispensed within the cell.

Referring to FIGS. 11–13 and focusing now on the body-form playback module 602, the body-form playback module 602 is formed as a three dimensional (3-D) physical model corresponding to the anatomy examined with the use of a PEM. For instance, body-form playback modules 602 may be formed to model the entire body, or any portion of interest thereof, such as the chest, abdomen, head, neck, arm, hand, leg, foot, pelvis, or finger. The illustrated embodiment of the body-form playback module 602 is shaped to emulate the abdominal section of a human body. Although preferably a body-form playback module 602 is used which corresponds to the anatomy of the PEM used in the original examination, a generic-body-form playback module may alternatively be used.

In the illustrated embodiment, the body form playback module 602 is molded from a soft, semicompliant material, such as a gel, nylon, rubber, silicon, or a soft plastic substrate. Each body-form playback module 602 preferably includes an elastic outer contact surface to simulate a skin surface 618.

The body-form playback module 602 includes an array 630 of cells 632. The cells 632 are similar to the cells 204 of the HCU 100 and PEM 200 described above. Although the sensory modulation subunit 506 described above both detect and generate a force, it will be apparent to one skilled in the art that the cells 632 of this embodiment may alternatively be constructed to apply a force alone, without the ability to detect a force. Such a configuration may be used to statically represent a form or condition of the body, such as the deformation of the abdominal cavity due to a fractured rib.

The overall size of the body-form playback module 602, and the number of cells 632 within each body-form playback module 602, may be selected to accommodate the desired application. Preferably, each cell 632 directly correlates in size and location with the cells 204 within the corresponding PEM 200. Of course the cells 602 will function generally opposite to the corresponding PEM cell 204. Conceptually, using photographic film processing as an analogy, the PEM would represent the negative while the body-form playback module 602 would represent the (positive) print.

Referring now to FIG. 13, each cell 632 includes a cavity 634 of several millimeters depth, corresponding to the size and dimension of a sensory modulator subunit in the corresponding PEM. Housed within each cavity 634 is a sensory modulation subunit 636. The top of the sensory modulation subunit 636 includes a slab 638 formed from a simulated skin material such as silicon rubber, a soft plastic matrix, or other suitable material, including, for example, natural, artificial, or biomaterials (artificial, simulated, cultured or engineered skin cells or substitutes). Each slab 638 is preferably on the order of fingertip size. To increase the sensitivity and functionality of the device, each cell 632 may be subdivided and each cavity 634 may represent a collection of smaller functional sensory modulation subunits.

A representative sensory modulation subunit 636 will now be described in detail. The subunit 636 includes a one-way pressure transducer 640 embedded within the slab 638 of simulated skin. A working surface 642 or pressure receiving face of the transducer 640 is oriented upward, i.e., in the direction facing the user's hand. The orientation of the transducer 640 is such that incoming pressure from the user will face the working surface 642 of the pressure transducer 640.

The slab 642 of simulated skin with the embedded pressure transducer 640 is then mounted on a support platform 644 formed from a rigid material, such as metal or plastic. Attached to the undersurface of the support platform 644 is a variable pressure producing device, which in the illustrated embodiment, is a single channel piston-type variable resistor 646. The piston resistor 646 provides counter pressure or a resistance force against the undersurface of the slab 638 of simulated skin dependent upon the response signal received from the data manipulation system 628. The components of each cell 632, including the slab 638, pressure transducer 640, support platform 644, and piston resistor 646, are located and supported within each cell cavity 634. Holes 648 are provided in each cavity 634 to accommodate insertion of the free end of the piston resistor 646. In the disclosed embodiment, the holes 648 are sized so that the support platform 644 is slightly elevated from the lower surface of the cavity 634 and therefore the only resistance felt by the user is that of the simulated skin slab 638 itself.

Preferably, each cell 632 includes a second pressure transducer 650 disposed at the interface of the support platform 644 and the bottom surface of the simulated skin slab 638. The second pressure transducer 650 is preferably oriented with a working surface 652 facing away from the bottom surface 654 of the simulated skin slab 638. The function of the second pressure transducer 650 is to monitor internal resistance and determine whether the proper amount of driving force is being maintained within each cell 632. This data is used to ensure that the appropriate resistance pattern is recreated when the surface of the body-form playback module is touched and manipulated, for example by the hands 605 of a user.

Alternatively, rather than a piston-resistor system, each cell 632 may be constructed using a system of linear actuators, motors, and/or optical encoders to produce and maintain a selected force and pressure profile within each cell 632. For example, referring to FIG. 14, the piston resistor 646 of FIG. 13 may be replaced with a mechanical actuating system 680. The mechanical actuating system 680 includes a linear actuator 656 comprised of a stepper motor 684 operable to drive a linear gear rack 688. The stepper motor 684 includes a gear 686 for engaging and selectively driving the gear rack 688 along its length. Attached upon the distal end of the gear rack 688 is a support platform 644. Thus, as should be apparent to one skilled in the art, the stepper motor 684 may be selectively controlled to drive the gear rack 688 and attached support platform 644 in a linear manner to adjust the pressure or resistance force exerted against the undersurface of the slab 638. The pressure or resistance force exerted is dependent upon the response signal received from the data manipulation system. Although a specific embodiment of a linear actuator 656 is depicted in the illustrated embodiment, it should be apparent to one skilled in the art that other linear actuators well known in the art and operable to linearly drive the support platform 644 are suitable for use with the present invention.

The mechanical actuating system 680 preferably includes an optical encoder 682. The optical encoder 682 includes a gear 690 disposed to engage the gear rack 688 in such a manner that any linear movement of the gear rack 688 causes a related rotation of the gear 690. Thus, the optical encoder 682 may be used to monitor the position of the gear rack 688 and thus indirectly monitor forces at the interface of the outer surface of the slab 638.

Figure 14:
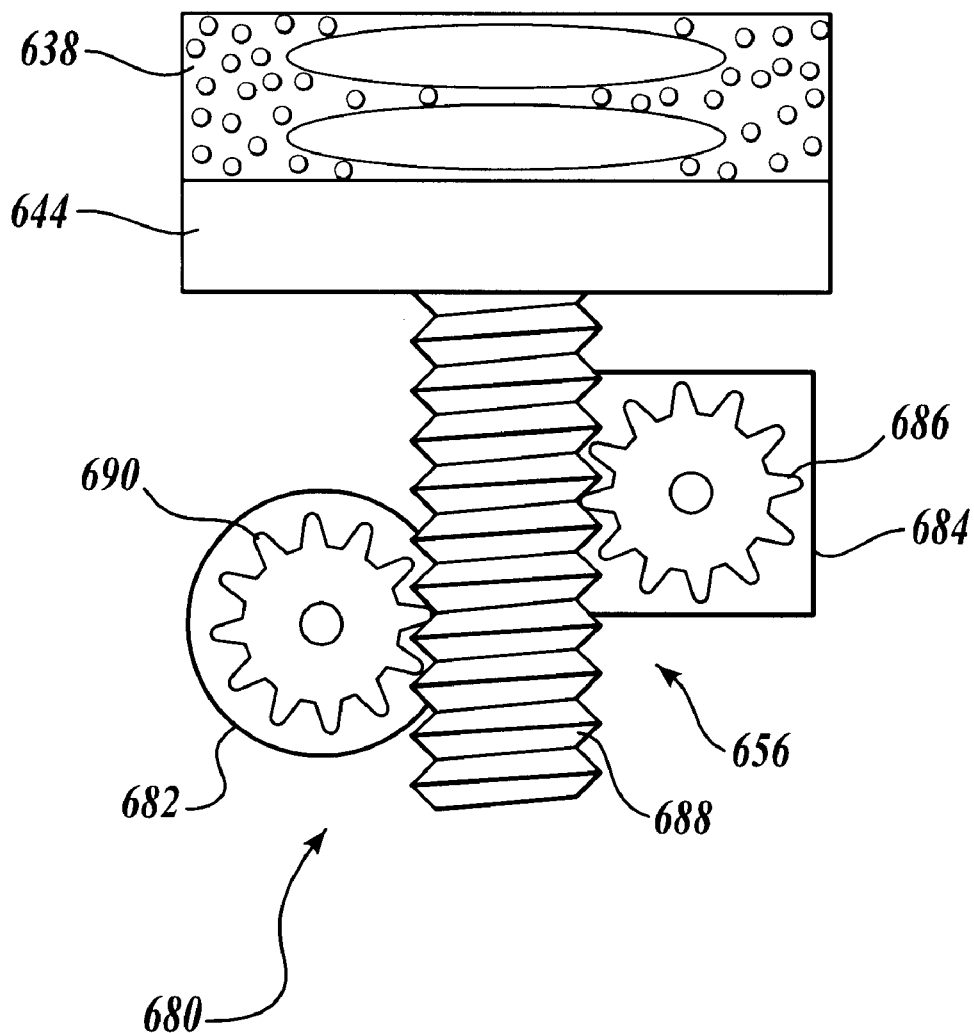
FIG. 14 is an elevation view of an alternate embodiment of a sensory modulation subunit formed in accordance with the present invention and suitable for use in the body-form playback module depicted in FIGS. 11 and 12.
Figure 15:
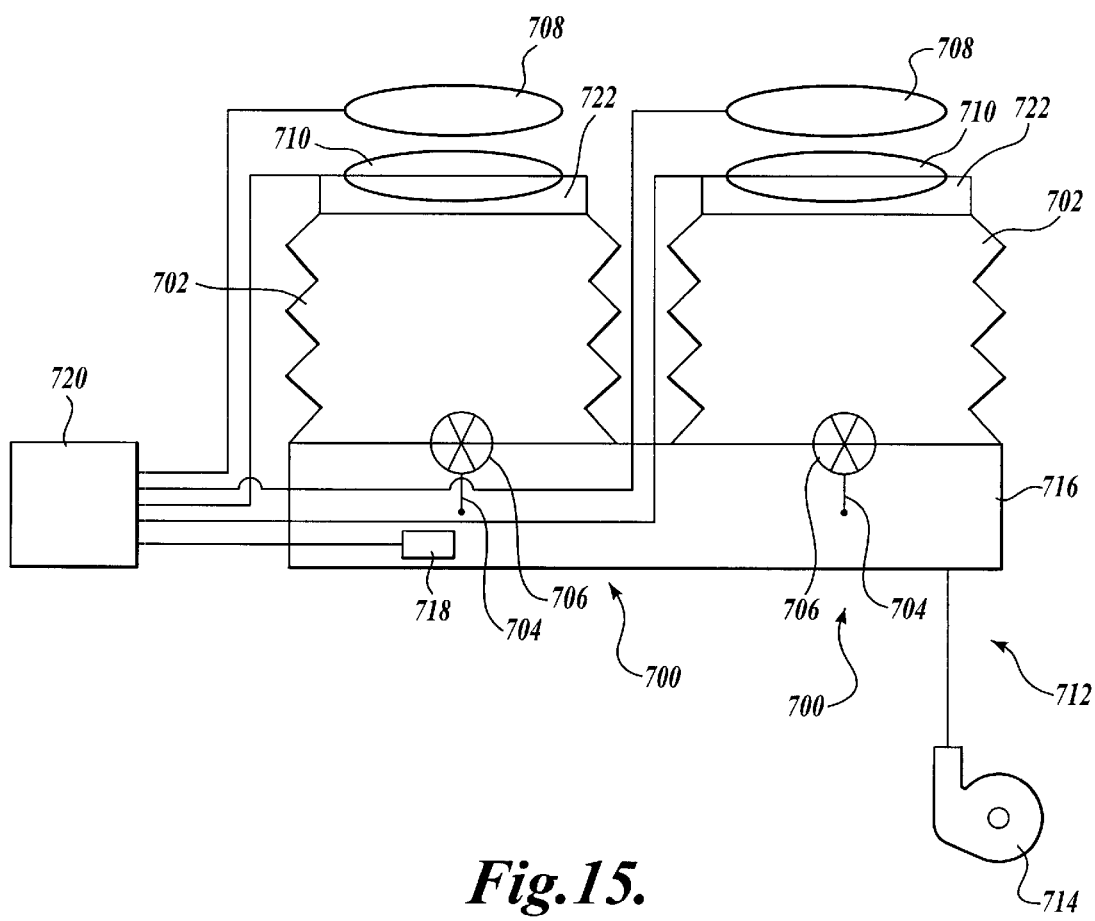
FIG. 15 is an elevation view of an alternate embodiment of a pair of sensory modulation subunits formed in accordance with the present invention and suitable for use in the body-form playback module depicted in FIGS. 11 and 12.

Referring now to FIGS. 13–15, other sensory modulation subunit configurations are contemplated by the present invention. For instance, sensory modulation subunits incorporating single or multiple, multi-channel pressure transducer or resistors within each cell are suitable for use in the present invention. In such a configuration, the absolute change in pressure or resistance is determined by taking the aggregate of forces applied by the single or multiple, multichannel pressure transducer or resistors.

Referring to FIG. 11, the body-form playback module 602 of the illustrated embodiment is coupled to the end-user's computer 606 via a conventional cable 612.

Referring to FIG. 15, an alternate embodiment of cells 700 suitable for use in the above described simulator assembly are shown. In this alternate embodiment the cells 700 utilize a pressurized fluid media, such as air, water, electrochemical gel, or hydraulic fluid, to linearly displace a support platform 722.

Each cell 700 includes an expansion chamber 702 with one, dual function intake/outlet line 704 to permit the influx and out flux of a pressurized fluid media. A valve 706 regulates the inflow and outflow of the pressurized fluid media into and out of the expansion chamber 702. Each cell 700 also includes a first single channel pressure transducer 708 and a second single channel pressure transducer 710. The first transducer 708 is oriented with its working surface facing outward and the second transducer 710 is oriented with its working surface facing inward toward the expansion chamber 702. The pressure transducers 708 and 710 function to maintain a desired expansion chamber 702 pressure to simulate the resistance found in a specific portion of a body area during an examination as well as monitor and record the user's applied palpation pressure.

The intake/outlet line 704 for each cell 700 is preferably connected to a storage chamber 716 for housing the pressurized fluid media. The valves 706 regulate flow of the pressurized fluid media between the expansion chambers 702 of each cell 700 and the storage chamber 716. Flow into the expansion chambers 702 causes the expansion chambers 702 to expand, thereby increasing the simulated resistance. Similarly, flow from the expansion chambers 702 causes the expansion chambers 702 to contract, thus decreasing the simulated resistance.

A pressurization assembly 712 includes a conventional pressurization device such as a pump 714 coupled to the storage chamber 716 for providing a pressurized fluid media to the storage chamber 716. Preferably, the pressurization assembly 712 and related control hardware is integrated directly into the body-form playback module, although it may be located externally.

Body-form playback modules utilizing air as a pressurized fluid media, for example, may utilize a semiclosed circuit design wherein the pump 714 draws air from outside the body-form playback module into the storage chamber 716 disposed underneath the array of cells 700. In the preferred embodiment, a plurality of valves 706 are disposed within the storage chamber 716 with each cell 700 having a single valve 706 associated with the expansion chamber 702 of each cell 700. Thus, the valve 706 may be selectively actuated to control the flow of the pressurized fluid media between the storage chamber 716 and the expansion chamber 702 of each cell. The single storage chamber 716 is therefore in direct communication with each expansion chamber 702 via the intervening valves 706.

A pressure regulating circuit 718 is preferably integrated into the storage chamber 716 to sense internal chamber pressure and transmit that information to a controller 720 for maintaining the desired storage chamber pressure. After the appropriate expansion chambers 702 are pressurized, the desired storage chamber 716 pressure achieved (corresponding to the appropriate applied pressure signal from the HCU) the resulting patient response signal is transmitted back to the HCU via the controller 720. If need be, the storage chamber 716 is vented into the atmosphere to reduce the pressure of the pressurization medium contained within the storage chamber 716. Body-form playback modules utilizing a hydraulic pressurized fluid media would consist of a self-contained, closed fluid system circuit, the construction of which should be apparent to one skilled in the art in light of the above disclosure.

Referring to FIG. 11, the function of the body-form playback module 602 is to recreate the internal patterns of resistance and pressures derived and recorded from the use of the above-described HCU and PEM units to provide a user a current live representation of the tactile feel of a portion of a patient's body felt at a remote time or location. The body-form playback module 602 may subsequently be physically manipulated, for example by another user to feel the simulated tactile sensations that were felt by an examiner during the original exam.

Although the above illustrated embodiment of the present invention is described with regard to a specific medical application for illustrative purposes, one skilled in the relevant art will appreciate that the disclosed first alternate embodiment is illustrative in nature and should not be construed as limited in application to the recreation of the actual physical findings associated with a physical examination. It should therefore be apparent to one skilled in the art that this alternate embodiment has wide application, and may be used in any situation requiring tactile information or three-dimensional modeling of a physical structure required by an individual in a non-contiguous location. For example, the embodiments formed in accordance with the present invention are suitable for use in non-medical applications, such as use in scientific applications (such as archeology or biology) where the field scientist may need or wish to transmit tactile properties of their discoveries/works back to colleagues at their parent organization. Thus, the embodiments formed in accordance with the present invention are suitable for use with items other than the human body, such as non-living objects.

Second Alternate Embodiment

Figure 16:
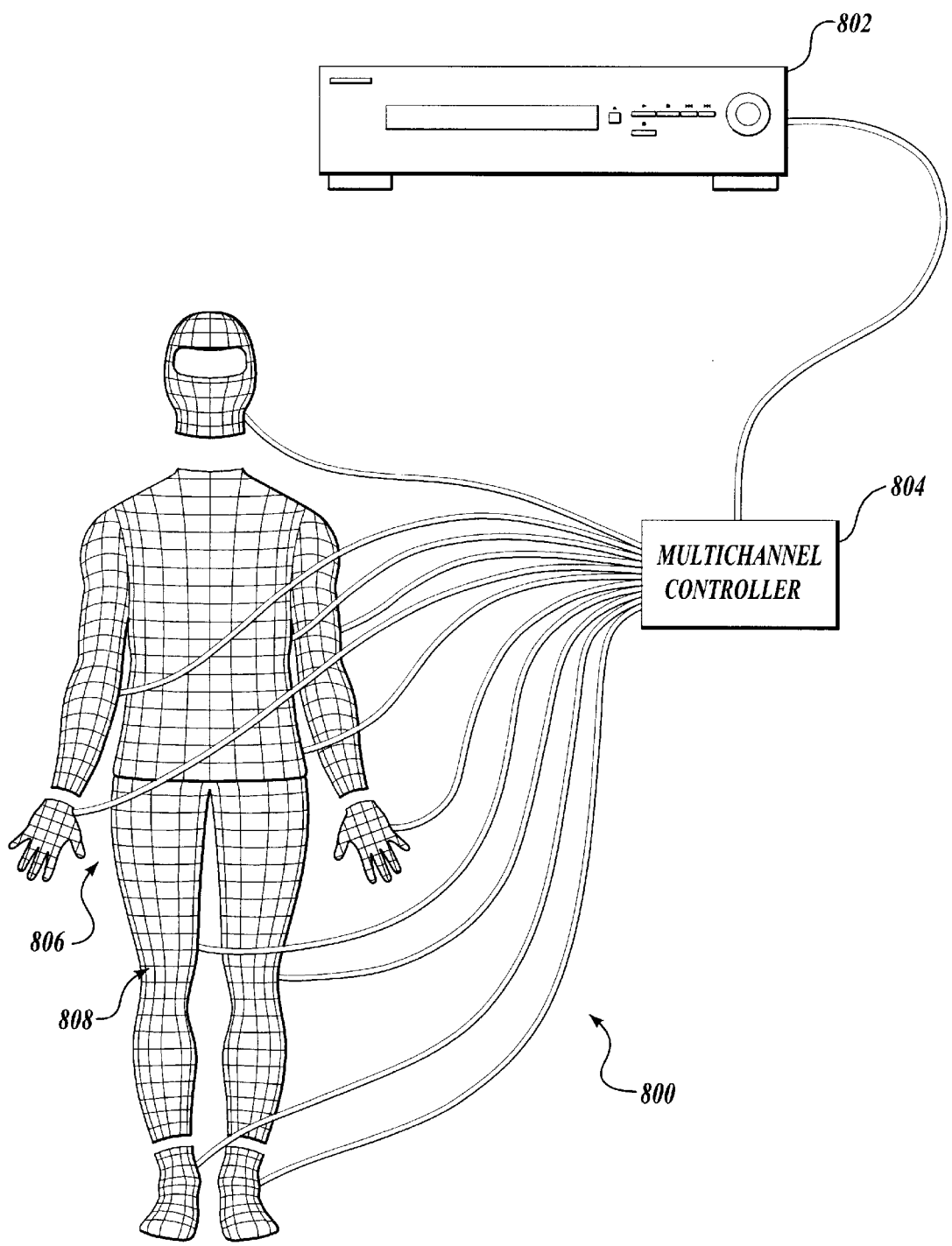
FIG. 16 is an elevation view of a second alternate embodiment formed in accordance with the present invention, the alternate embodiment generally referred to as a tactile playback assembly, the tactile playback assembly including a playback device, a multichannel controller, and an interactive pressure playback garment.

In another embodiment of the present invention, suitable for use in the entertainment industry, tactile data is integrated into entertainment media, such as DVDs, CDs, computer games, and TV broadcasts to bring the sense of touch into prerecorded movies, audio, and video formats. Referring to FIG. 16, a tactile playback assembly 800 is shown. The tactile playback assembly 800 includes a playback device 802, a multichannel controller 804, and an interactive pressure playback garment 806.

The playback device 802 of the illustrated embodiment is similar to a DVD player in appearance and operation. However, it will be apparent to one skilled in the art that the playback device 802 may take any suitable form operable to translate stored data, for example digital data, into control signals usable by the interactive pressure playback garment 806. For example, any playback devices 802 operable to take a media storage device, such as a CD, digital tape-DAT, MP3 file, hard drive unit, etc., and translate digitally encoded tactile data stored thereupon for transmission to the interactive pressure playback garment 806 worn by the consumer/user is suitable for use with the present invention. The interactive pressure playback garment 806 may be substantially similar in construction and operation to the PEM devices already described in the above embodiments. The interactive pressure playback garment 806 may alternatively cover the entire body of the user as illustrated, or only a portion of the user, such as the chest, abdomen, arms, hands, legs, feet, etc.

In operation, the interactive pressure playback garment 806 receives digitally encoded tactile data sent from the playback device 802, converts the data to input signals for driving a plurality of variable pressure producing devices housed in an array of cells 808 disposed in the interactive pressure playback garment 806. The pressure producing devices are selectively actuated to apply a desired force or tactile sensation upon the user donning the interactive pressure playback garment 806. The pressure producing devices are described above and therefore will not be described here. However, it will be appreciated that the interactive pressure playback garment 806 may be simplified so that the cells of the garment 806 are operable to apply a force alone, without the ability to detect a force. Thus, one of the pressure transducers described above may be eliminated if a simplified interactive pressure playback garment 806 is desired.

The tactile playback assembly 800 permits tactile information to be encoded and incorporated along with current audio and video information and applied to all forms of entertainment media, including computer games, film, and internet based audio/video transmissions. Incorporation of tactile event data into a DVD film track, for example, would allow the consumer to experience some of the tactile feel of the displayed action. Examples include being able to feel a hand being put on the shoulder of a character from behind them during a horror or mystery story, or the ability to feel a punch or kick sustained by a character in an action movie. As should be apparent to one skilled in the art, similar applications may also be incorporated into computer games, and other forms of entertainment media. As should also be apparent to one skilled in the art, the playback device 802 may be operable to transmit data over a communications network to a playback garment 806 located in a non-contiguous location.

Third Alternate Embodiment

Figure 17:
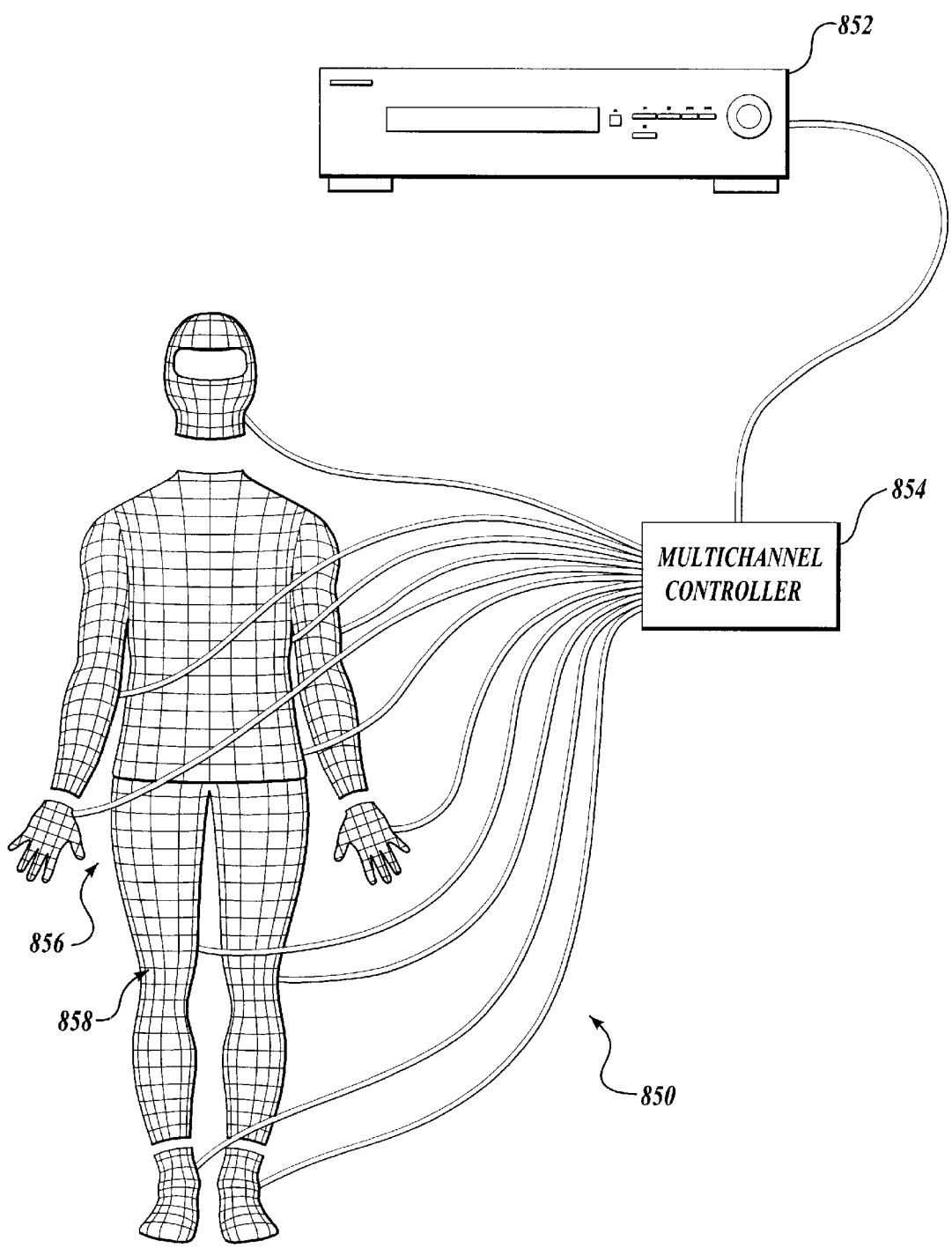
FIG. 17 is an elevation view of a third alternate embodiment formed in accordance with the present invention, the alternate embodiment generally referred to as an entertainment recording assembly, the entertainment recording assembly including a recording device, a multichannel controller, and an interactive pressure recording garment.
Figure 18:
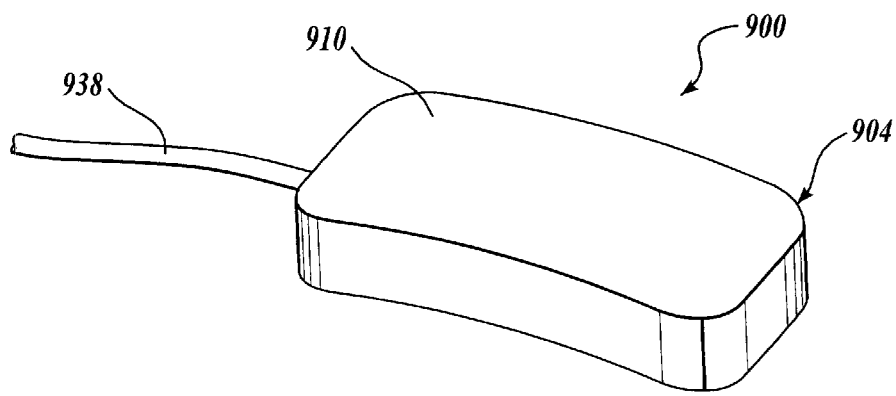
FIG. 18 is a perspective view of a fourth alternate embodiment formed in accordance with the present invention, the alternate embodiment generally referred to as an imaging exam assembly.
Figure 19:
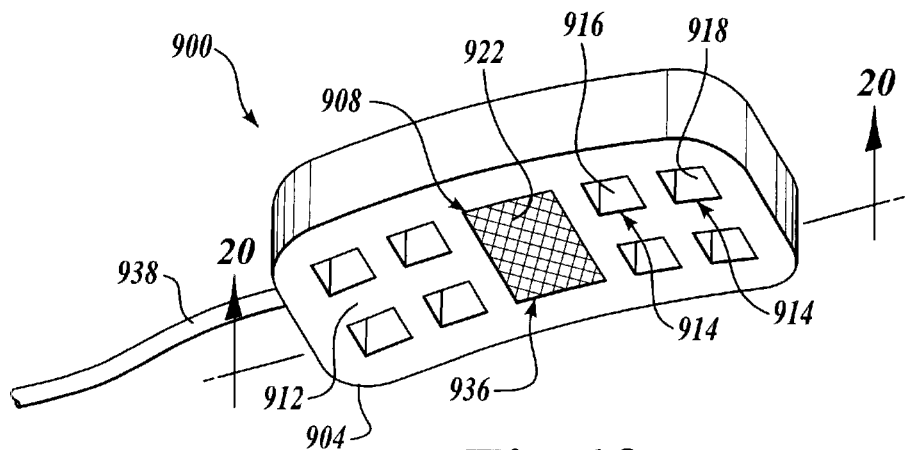
FIG. 19 is a perspective view of the imaging exam assembly depicted in FIG. 18, showing the bottom of the imaging exam assembly.
Figure 20:
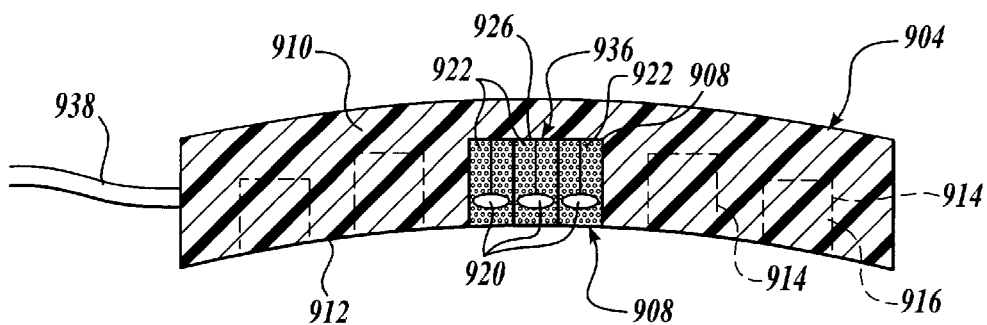
FIG. 20 is a cross-sectional view of the imaging exam assembly depicted in FIG. 19, the cross-sectional cut taken substantially through Section 20—20 of FIG. 19.

Referring to FIG. 17, a third alternate embodiment formed in accordance with the present invention is described as a tactile recording assembly 850. The tactile recording assembly 850 includes a recording device 852, a multichannel controller 854, and an interactive pressure recording garment 856.

The recording device 852 stores digitally encoded tactile data received from the interactive pressure recording garment 856 on a media storage device. The recording device 852 of the illustrated embodiment is similar to a DVD recorder in appearance and operation. In a preferred use, the interactive pressure recording garment 856 is donned by a user, for example an actor or a stunt person. The interactive pressure recording garment 856 is then impacted by an external force, for example by a second actor or stunt person. The tactile forces exerted upon the interactive pressure recording garment 856 are then recorded by the recording device 852 which is coupled in signal communication with the interactive pressure recording garment 856. Thus, a digital data file may be created which may then be played back by the playback device 802 upon the interactive pressure playback garment 806 of the alternate embodiment depicted in FIG. 16.

In operation, the interactive pressure recording garment 856 receives tactile forces upon a plurality of sensory modulation subunits housed with an array of cells 858, converts the tactile forces received to output signals, and sends the output signals to a multi-channel controller 854. The sensory modulation subunits are capable of generating output signals of variable magnitudes such that the magnitudes of the output signals correlate to the magnitude of the tactile force applied to the sensory modulation subunits. The multi-channel controller 854 processes the signals received from the interactive pressure recording garment 856 and transmits the processed signals to the recording device 852 for storage. The sensory modulation subunits of the interactive pressure recording garment 856 are substantially similar in construction and operation to the sensory modulation subunits of the PEM devices described in the above embodiments and therefore will not be described in further detail herein. Although the interactive pressure recording garment 856 is depicted as covering the entire body of the user, it should be apparent to one skilled in the art that the interactive pressure recording garment 856 may alternatively cover any portion thereof, such as the chest, abdomen, arms, hands, legs, feet, etc., of the user.

Referring to FIGS. 16 and 17, although in the preferred embodiment the digital data file is created through the donning of the interactive pressure recording garment 856, it should be apparent to one skilled in the art that the data file may also be generated by other means, such as by computer generating the digital data file without the aid of the interactive pressure recording garment 856. Further still, it should be apparent that the interactive pressure playback garment 806 may be coupled directly to the interactive pressure recording garment 856 in a contiguous location, or coupled through a communications network, such as through a global computer network, when the garments 806 and 856 are located in non-contiguous locations. Thus, a first user wearing the interactive pressure playback garment 806 may feel the tactile forces received by a second user wearing the interactive pressure recording garment 856.

Fourth Alternate Embodiment

Illustrated in FIGS. 18–21 is a fourth alternate embodiment formed in accordance with the present invention and generally referred to as an imaging exam assembly 900. The imaging exam assembly 900 permits a physical examination of a patient's body without actual direct physical contact between the patient and a physician. The imaging exam assembly 900 includes an imaging device 936 operable to simultaneously generate 2-D or 3-D internal or external body imaging. The imaging exam assembly 900 also obtains tactile data concurrently with the body imaging data. Thus, a physician/user would be able to remotely tactilely sense or manipulate the tissue or body in question and simultaneously view the internal and/or external impact of the applied tactile forces. This capability enhances the functionality of the device as a medical diagnostic instrument.

The imaging exam assembly 900 is comprised generally of three components: an HCU (not shown), a patient examination-imaging module 904 (hereinafter "PEIM") and computer software operable to control the acquisition, calibration, transfer, and translation of both the physical tactile information and the image processing data between the physician and the patient located in a non-contiguous location. The HCU is substantially identical to the HCU described above for the embodiment depicted in FIGS. 1–4, and therefore for brevity, will not be described herein.

The PEIM 904 is preferably a molded-plastic device formed generally in the shape of a rectangular solid with the size approximating that of a human hand. The advantages of this type of construction are its lightweight, ease of mobility, ease of manufacturing with respect to device shaping and form, durability, and impact resistance. Although the illustrated embodiment of the PEIM 904 is rectangular, it will be apparent to one skilled in the art that the PEIM 904 may be formed in any suitable shape. Preferably, however, the PEIM 904 is shaped to provide a comfortable contact surface between critical sensory, motor, and imaging portions of the device and the person or object being examined.

In the illustrated embodiment, the PEIM 904 has a slight rise in the top surface 910 while the bottom working surface 912 has a slight depression or concavity with respect to the periphery of the PEIM 904. The slight rise in the top surface 910 allows the patient to place their hand on the top of the PEIM 904 and hold it in place or move it along portions of their body as directed by the remotely located examining physician. Alternately, the PEIM 904 may be designed as a "glove" where the patient's whole hand may be inserted into the PEIM 904.

The bottom-working surface 912 of the PEIM 904 is divided into cells 914 that function as tactile sensory processors. The tactile sensory processing aspect of the PEIM 904 is substantially similar to the sensory processing aspect of the above-described embodiments, and therefore, will only be briefly described herein. Briefly, the cells 914 are formed by hollowing out a plurality of cavities 916 (typically several millimeters in depth) in the molded plastic of the PEIM 904. Within each cavity 916, a sensory modulation subunit 918 is housed. The electromechanical and/or pneumatic system architecture of the sensory modulation subunits 918 is unchanged from the sensory modulation subunits 918 described for the above embodiments, and therefore will not be repeated here.

The size of each sensory modulation subunit 918 will vary with the size of each cavity 916 in the PEIM 904. In general, the footprint of each sensory modulation subunit 918 will approximate the dimensions of a fingertip. In the illustrated embodiment, a 2×4 matrix of cells 914 housing eight sensory modulation subunits 918 is shown. The size, shape, and number of sensory modulation subunits 918 may vary to increase (or decrease, though not preferred) the sensitivity and functionality of the device. For example, in a preferred embodiment, the sensory modulation subunits 918 are formed in a 4×4 matrix housing sixteen sensory modulation subunits 918. Each sensory modulation subunit 918 may be subdivided and therefore, each cavity 916 may represent a collection of smaller functional sensory modulation subunits 918.

The imaging system functions of the PEIM 904 are preferably provided through an ultrasound imaging technology platform. In the illustrated embodiment of the PEIM 904, an imaging device 936 is disposed along the midportion of the bottom surface 912 of the PEIM 904. The imaging device 936 includes a linear array transducer 908 which has ultrasound signal generation and reception capabilities. The linear array transducer 908 includes multifunction transducers 920 that both send and receive signals using standard signal gating technology. A simulated skin surface 922, comprised of a non-interfering material, such as a gel matrix material, is disposed over the linear array transducer 908. Air interferes with the desired transmission of the ultrasonic waves, therefore, a gel matrix is applied at the interface between the linear array transducer 908 and the patient's skin. The linear array transducer 908 may vary in both configuration and frequency depending upon the desired functionality of the PEIM 904 and the depth of penetration required for the ultrasound. In general, devices used for imaging deep tissue structures will utilize a linear array transducer 908 with lower transmission frequencies while those with more superficial structures will utilize a linear array transducer 908 with higher frequency capabilities.

The PEIM 904 is contemplated to be used with the system software and the HCU described for the above embodiments. The PEIM 904 will be connected to a computer or communications device (not shown) at the patient's end. The patient will hold the PEIM 904 and move it along their body as directed by the physician. The physician may then use the HCU to transmit pressure signals to the PEIM 904 through a communications network. The PEIM 904 may then detect the patient's counter-pressure response, and transmit a resultant counter-pressure signal to the HCU.

In addition, the PEIM 904 may transmit and receive ultrasound pulse information. In the preferred embodiment, the send signal is transmitted via the communication network from the processing software on the physician side computer to activate the linear array transducer 908 within the PEIM 904 and the ultrasound signal is transmitted to the patient. Next, gating functions are performed and the same linear array transducer 908 receives the returning echoes. That information is transmitted back to the physician host computer.

In the illustrated embodiment, well known image processing may be used to provide B-mode, spectral, duplex, and/or color information. That information is preferably available in real time to the physician performing the examination over the communication network. As with the other functions of the imaging exam assembly 900, this digital information may be stored and played back, incorporating the tactile event data with the imaging data.

Additional device configurations may be utilized for the PEIM described above, such as configuring the PEIM as a wearable garment with the examination pad applied directly over the patient's body to be examined and held in place by a removable fastening assembly such as a hook and loop fastening assembly. The hook and loop fastening assembly would provide adjustability and allow for application to a wide variety of body shapes and sizes. The PEIM may be fashioned into vests for chest applications; binders for abdominal applications; sleeves, gauntlets, or gloves for upper extremity applications; pant legs or boots for lower extremity applications; or small strips for small applications such as fingers or toes. Additional versions may also include sensory modulation subunits based on hydraulic and pneumatic systems as previously described.

The PEIM 904 may be attached to a command control box (not shown) via an electrical umbilical 938 or directly into a patient end computer, or transmission device. The command control box would incorporate a well known power supply, a small central processing unit, a signal processor, digital to analog converter, and a communications system for the PEIM 904 in order for it to receive and transmit data, and be linked to the functions of the physician HCU.

The communications system may include an internal modem which would allow for connection to a communication network, a computer or direct connection to a land-based or direct wired telephone line or any other current or future device which would allow for (1) light-based/optical based communications including fiber-optic cable channels and non-fiber, light based methods of data/voice/visual signal transmission, (2) wireless communications including but not limited to radio frequency, ultrahigh frequency, microwave, or satellite systems in which voice and/or data information can be transmitted or received, and (3) any future methods of voice or data transmission utilizing any currently unused mediums such as infrared light, magnetism, other wavelengths of visible and non-visible radiation, biomaterials (including biorobots or viral vectors) or atomic/subatomic particles.

Preferably, this control section of the PEIM 904 would be disposed away from the patient to reduce the amount of weight applied directly to the patient to reduce the size of the PEIM, especially if the PEIM 904 is to be placed on a small section of the body such as a limb or finger, and/or to increase the safety of the unit (reduced RF or microwave radiation exposure from communications/data transmissions). As should be apparent to one skilled in the art, the electrical umbilical 938 may include contact wires disposed between the pressure transducers and variable force producing devices of the sensory modulation subunits, the imaging device 908 and the power supply.

As should be apparent to one skilled in the art, the PEIM 904 may also be configured with single or multiple, multi-channel pressure transducer/resistor devices wherein the absolute change in resistance is translated back to the user's hand via the HCU (not shown). To increase the sensitivity and functionality of the PEIM 904, each cell 914 may be subdivided and multiple sensory modulation subunits applied throughout the PEIM 904.

Figure 21:
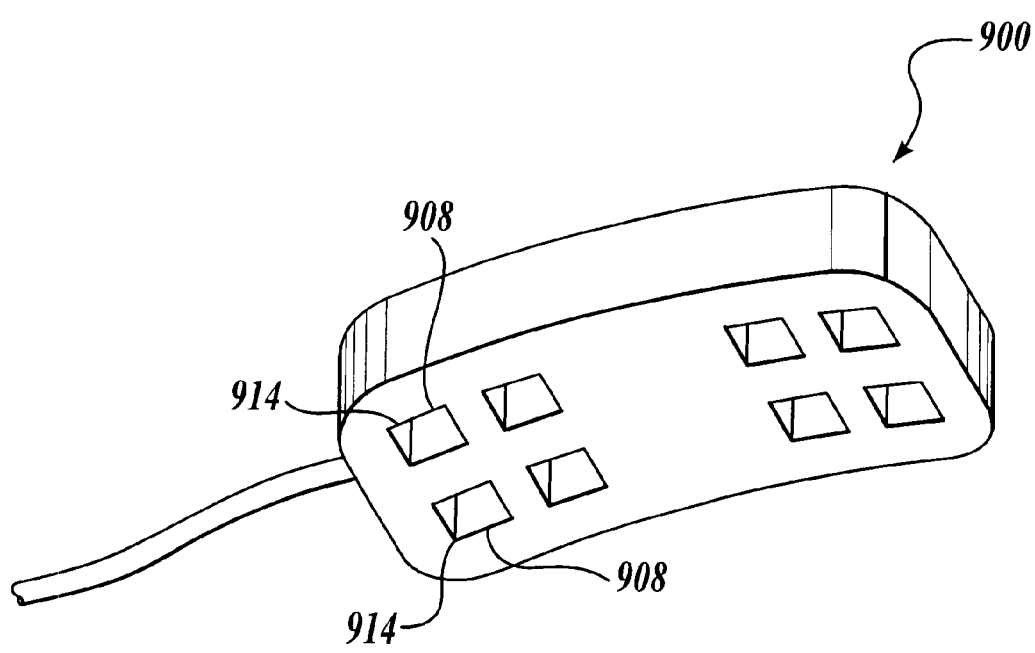
FIG. 21 is a perspective view of an alternate embodiment of the imaging exam assembly depicted in FIGS. 18–20.

Although in the above embodiment the linear array transducer 908 is disposed within the PEIM 904 separate from the cells 914 housing the sensory modulation subunits 918, it will be apparent to one skilled in the art that other configurations are possible and within the scope of the present invention. For example, as shown in FIG. 21, an ultrasound transducer 908 may be disposed within each cell 914, so that each cell 914 contains both a sensory modulation subunit and an ultrasound transducer 908.

Figure 22:
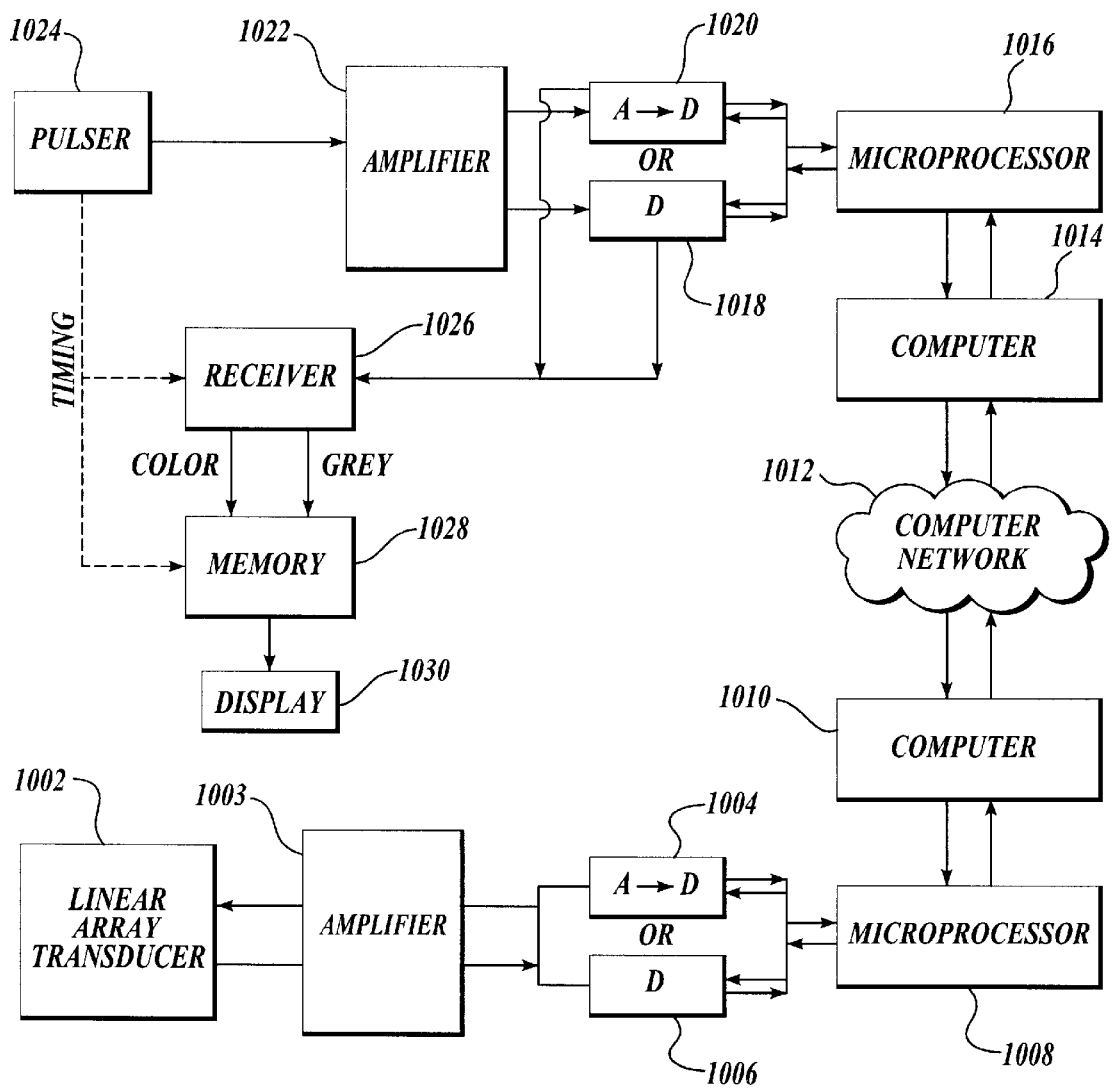
FIG. 22 is a general process flow diagram of the fourth alternate embodiment formed in accordance with the present invention and depicted in FIGS. 18–20.

FIG. 22 is a flow chart showing the overall process associated with the imaging exam assembly 900. Software controls the various functions of the HCU, PEIM, system dynamics, and communications protocols. The specific functions of the software 1000 are similar to those described for the earlier embodiments, except for the additional features related to the imaging aspects of the invention. Therefore, the following discussion focuses on those aspects utilized in controlling the imaging aspects of the PEIM 904, and will not describe in detail the functions of the software previously described above, for brevity.

The additional software functions include all of the ultrasound signal transmission, gating, and communications protocols as well as the specific signal processing functions, signal analysis, and processing commands to provide B-mode, spectral analysis, color, and/or duplex Doppler images. The software controls the device transmission protocols for the raw send and receive data using a communication network located between the working portions of the linear array transducer 908 and the remainder of the PEIM 904 providing the tactile data.

Referring to FIG. 22, a computer 1014 generates a send signal based upon receipt of a pulse from a pulser 1024. The send signal is received by a microprocessor 1016, that may be integrally formed with the computer 1016. The send signal is processed by the software and transmitted over a computer network 1012, for example a global computer network, to a linear array transducer 1002 as either a digital signal or an analog signal, depending on whether the send signal passes through the digital gate 1006 or a digital to analog conversion gate 1004. The linear array transducer 1002 receives and processes the send signal and generates an ultrasound wave in response to the received send signal. The ultrasound wave is directed into the body of the patient. Returned ultrasonic waves received by the linear array transducer 1002 are processed and transmitted to the microprocessor 1008 via the digital gate 1006 or the analog to digital conversion gate 1004, as appropriate. The microprocessor 1008 processes the received signal and transmits the signal to the computer 1010. The computer 1010 processes the received signals and transmits the processed data representing the ultrasound images over a communication network 1012, to the second computer 1014.

The computer 1014 processes the received data and transmits data to the microprocessor 1016 then through digital gate 1018 or a digital to analog conversion gate 1020 to a receiver 1026. The receiver 1026 processes the received data for utilization in a gray scale display unit or a color display unit and transmits the data to a memory unit 1028 and, preferably to a display unit 1030. The display unit 1030 presents the data in visual form for use by the user/physician.

The pulser 1024 synchronizes the various components of the depicted system. More specifically, as is well known in the art, ultrasound imaging devices transmit for a brief period an ultrasound wave. The transmit function of the transducer is then turned off, and the ultrasound transducer then listens for a return echo for a brief period. The pulser 1024 transmits a timing pulse to trigger and synchronize the various events conducted during the ultrasound imaging process.

The pulser 1024 of the illustrated embodiment of the present invention is coupled in signal communication with the memory unit 1028, receiver 1026, and an amplifier 1022. Once a pulse is received by the amplifier 1022 from the pulser 1024, the amplifier 1022 generates an output signal in the form of a voltage that is directed to either the digital gate 1018 or the analog to digital conversion gate 1020, for transmission to the microprocessor 1016. The signal is processed in the microprocessor 1016 and transmitted to the computer 1014. The computer further processes the signal and transmits the signal upon a communication network, such as the internet 1012, to another computer 1010. The computer 1010 processes the signal, and transmits the signal to the microprocessor 1008 for further processing. The microprocessor 1008 then transmits the signal to either a digital gate 1006 or to a digital to analog gate 1004 for transmission to the transducer array 1002 preferably through a signal amplifier 1003. Depending upon the signal received by the transducer array 1002, the transducer array 1002 will either assume a transmit or receive configuration.

Although the embodiments of the present invention are described with regard to a specific medical application for illustrative purposes, one skilled in the relevant art will appreciate that the disclosed alternate embodiments are illustrative in nature and should not be construed as limited in application to the recreation of the actual physical finding associated with a physical examination. It should be apparent therefore that the alternate embodiments have wide application, and may be used in any situation requiring tactile information or three-dimensional modeling of a physical structure required by an individual in a non-contiguous location.

For example, although the illustrated embodiment of the present invention is described as operable to simulate a physical examination of a patient in a remote location, additional applications within the field of medicine would include the ability to examine a patient in hostile environments, such as deep sea, space, battle field conditions, remote locations, mountain/jungle expeditions, while incorporating tactile examination as well as real time internal imaging capabilities. Further, portable versions could also be applied in a medical station within the workplace, obviating the necessity of a patient having to actually leave work and travel to a physician's office. This is both very inefficient for both the patient and the physician. Portable versions could also be applied in the home where some evaluations could preclude the need for after-hours trips to the emergency room. This efficiency would have a significant effect on overall health care costs. Further, the illustrated embodiments may be applied to other scientific applications (such as archeology, biology, deep sea) where the field scientist may need or wish to transmit tactile and internal image properties of their discoveries/works back to colleagues at their parent organization.

While the preferred embodiment of the invention has been illustrated and described, it will be appreciated that various changes can be made therein without departing from the spirit and scope of the invention.

The embodiments of the invention in which an exclusive poperty or privilege is claimed are defined as follows:

1. A stimulator assembly for simulating the tactile response of a real item, the simulator assembly comprising:
   (a) a playback module having a data file generated from a tactile examination of the real item, the playback module uses the data file to simulate tactile characteristics of the real item, wherein the playback module is formed generally in the shape of at least a portion of the real item, the playback module including an outer skin;
   (b) a plurality of cavities disposed in the playback module and beneath the outer skin; and
   (c) a plurality of sensory modulation subunits, each sensory modulation subunit disposed at least partially within one of the plurality of cavities, each sensory modulation subunit exerts a force against the outer skin in response to a received input signal wherein the received input signal is responsive to a force applied to the playback module.

2. The simulator assembly of claim 1, wherein the sensory modulation subunits further comprise a pressure transducer adapted to generate an output signal in response to an applied force.

3. The simulator assembly of claim 2, further comprising a computer system functionally connected to the sensory modulation subunits, wherein the computer system transmits the input signals to dynamically control the forces exerted by the sensory modulation subunits.

4. The simulator assembly of claim 3, wherein the computer system further receives the output signals generated by the sensory modulation subunits and further wherein the received output signals are used to determine the sensory modulation subunits input signals.

5. The simulator assembly of claim 4, wherein the computer system further comprises a memory module containing data defining the firmness of the simulated item and wherein the data is used to determine the sensory modulation subunit input signals.

6. The simulator assembly of claim 4, wherein the sensory modulation subunits comprise a piston-type variable resistor.

7. The simulator assembly of claim 4, wherein the sensory modulation subunits comprise a linear actuator.

8. The simulator assembly of claim 7, wherein the sensory modulation subunits further comprise an optical encoder that detects movement of the linear actuator and generates a responsive signal.

9. The simulator assembly of claim 4, wherein the sensory modulation subunits comprise an expansion chamber adapted to receive a pressurizing fluid.

10. The simulator assembly of claim 9, further comprising a reservoir of pressurizing fluid and wherein a plurality of sensory modulation subunits are fluidly connected to the reservoir with a valve.

11. The simulator assembly of claim 1, wherein the simulated item is a portion of a human body.

12. The simulator assembly of claim 11, wherein the data file comprises a portion of patient medical record.

13. A device for remotely conducting a direct manual examination of a patient comprising:
   (a) a hand control unit having at least one first sensory modulation subunit that:
      (i) detects a force applied to the first sensory modulation subunit and generates a first signal in response to the detected force, and
      (ii) exerts a force in response to a received second signal;
   (b) a patient examination module, the patient examination module having a plurality of second sensory modulation subunits that are selectively connectable to the first sensory modulation subunit, such that:
      (i) the second sensory modulation subunit receives the first signal and exerts a force in response to the received first signal, and
      (ii) detects a force resisting the exerted force and generates the second signal based on the detected resisting force, the second signal being received by the first sensory modulation subunit; and (c) a recording device in signal communication with the first and second sensory modulation subunits that records the first and second signals into a medical record such that the direct manual examination may be simulated at a later time.

14. The device of claim 13, wherein the first sensory modulation subunit is coupled in signal communication with a first computer, wherein the second sensory modulation subunit is coupled in signal communication with a second computer, and wherein a communication network operatively connects the first computer with the second computer.

15. The device of claim 14, wherein the communication network operates over a global telecommunication network.

16. The device of claim 13, wherein the hand control unit and the patient examination module are in non-contiguous locations.

17. A method of recording a medical record comprising the steps of:
   applying a sensor array to a patient that is detects the tactile response of the patient to an applied external force;
   applying an external force to the patient; and
   recording the tactile response of the patient to the applied external force such that the tactile response can be replayed in a tactile simulator assembly.

* * * * *

UNITED STATES PATENT AND TRADEMARK OFFICE
CERTIFICATE OF CORRECTION

PATENT NO. : 6,726,638 B2  Page 1 of 1
DATED : April 27, 2004
INVENTOR(S) : M.P. Ombrellaro It is certified that error appears in the above-identified patent and that said Letters Patent is hereby corrected as shown below:

Title page,
Item [73], Assignee, "Cel-Kom LLC," should read -- CEL-KOM LLC, --
Item [74], Attorney, Agent, or Firm, "O'Connor;" should read -- O'Connor --

Column 29,
Line 58, "inventionin" should read -- invention in --
Line 59, "poperty" should read -- property --

Column 32,
Line 6, "that is detects" should read -- that detects --

Signed and Sealed this

Twenty-eighth Day of September, 2004

JON W. DUDAS
*Director of the United States Patent and Trademark Office*